US006024938A

United States Patent [19]
Corbo et al.

[11] Patent Number: 6,024,938
[45] Date of Patent: Feb. 15, 2000

[54] LYOPHILIZED IMAGING AGENT FORMULATION COMPRISING A CHEMOTACTIC PEPTIDE

[75] Inventors: Diane C. Corbo, Flemington; Mary Jean M. Link, Princeton, both of N.J.; N. Adeyinka Williams, Doylestown; Michelle L. Tomsho, Langhorne, both of Pa.; Michael Bornstein, Westfield, N.J.; Howard F. Solomon, New Hope; Scott K. Larsen, West Chester, both of Pa.; Robert L. Suddith, Wilmington, N.C.

[73] Assignees: Ortho Pharmaceutical Corporation, Raritan, N.J.; Johnson-Matthey Inc., West Chester, Pa.

[21] Appl. No.: 08/997,894

[22] Filed: Dec. 24, 1997

Related U.S. Application Data

[62] Division of application No. 08/271,818, Jul. 7, 1994, abandoned.

[51] Int. Cl.$^7$ .......................... A61K 51/00; A61M 36/14
[52] U.S. Cl. .................. 424/1.69; 530/300; 530/331; 424/1.11; 424/1.65; 424/9.1
[58] Field of Search .................................. 424/1.11, 1.65, 424/1.69, 9.1, 9.3, 9.4, 9.5, 9.6, 1.49, 184.1; 530/300, 324–331; 534/7, 10–16; 206/223, 569, 570

[56] References Cited

U.S. PATENT DOCUMENTS

| | | | |
|---|---|---|---|
| 4,926,869 | 5/1990 | Rubin et al. | 128/654 |
| 5,350,837 | 9/1994 | Bridger et al. | 534/14 |
| 5,670,133 | 9/1997 | Zamora | 424/9.1 |
| 5,700,444 | 12/1997 | Zamora et al. | 424/1.69 |
| 5,759,515 | 6/1998 | Rhodes et al. | 424/1.69 |
| 5,792,444 | 8/1998 | Fischman et al. | 424/1.69 |
| 5,807,538 | 9/1998 | Dean et al. | 424/1.69 |

FOREIGN PATENT DOCUMENTS

| | | |
|---|---|---|
| 0 314 317 A1 | 5/1989 | European Pat. Off. . |
| WO 89/11297 | 11/1989 | WIPO . |
| WO 91/04056 | 4/1991 | WIPO . |

OTHER PUBLICATIONS

Tschopp, J., "Kinetics of Activation of the First Component of Complement (C1) by IgG Oligomers," *Mol. Immunol.* 19(5):651–657 (1982).
Vandenberg, E., et al., "Protein Immobilization to 3–Aminopropyl Triethoxy Silane/Glutaraldehyde Surfaces: Characterization by Detergent Washing," *J. Colloid & Interface Sci.* 143(2):327–335 (1991).
Vnek, J., et al., "Association of Normal Serum Protein Antigens With Chimpanzee Hepatitis B Surface Antigen Particles," *J. Med. Virol.* 2:319–333 (1978).
Zav'yalov, V.P., et al., "Temperature and pH Dependent Changes of Immunoglobulin G Structure," *Biochim. Biophys. Acta* 386:155–167 (1975).
The Merck Index, 10$^{th}$ Ed., Windhulz, M., et al., eds., Merck & Co., Inc., pub., Rahway, N.J., p. 1095 (No. 7455) (1983).

Rubin, R.H., et al., "$^{111}$In–Labeled Nonspecific Immunoglobulin Scanning in the Detection of Focal Infection," *N. Engl. J. Med.* 321(14):935–940 (1989).
Schwartz, D.A., et al., "Preparation of Hydrazino–Modified Proteins and Their Use for the Synthesis of $^{99m}$Tc–Protein Conjugates," *Bioconjugate Chem.* 2(5):333–336 (1991).
Shapshak, P., et al., "Quantitation of Human Immunoglobulin G and Albumin in Electroimmunodiffusion Gels Containing Ionic and Nonionic Detergents, " *Anal. Biochem.* 132:305–311 (1983).
Prince, A.M., et al., "A New Hepatitis B Vaccine Containing HBeAg in Addition to HBsAg," *Develop. Biol. Standard.* 54:13–22 (1983).
Prince, A.M., et al., "An Affordable Multideterminant Plasma–Derived Hepatitis B Virus Vaccine, " *IARC Scientific Publications* 63:355–372 (1984).
Rosenqvist, E., et al., "Thermal Properties of Human IgG," *Mol. Immun.* 24(5):495–501 (1987).
Nolte, F.S., and Kapral, F.A., "Immunogenicity of *Staphylococcus aureus* Delta–Toxin," *Infection and Immunity* 31(3):1251–1260 (1981).
Oreskes, I., and Mandel, D., "Size Fractionation of Thermal Aggregates of Immunoglobulin G," *Anal. Biochem.* 134:199–204 (1983).
Oyen, W.J.G., et al., "Scintigraphic Detection of Bone and Joint Infections with Indium–111–Labeled Nonspecific Polyclonal Human Immunoglobulin G," *J. Nucl. Med.* 31(4):403–412 (1990).
Merrifield, R.B., "Solid Phase Peptide Synthesis. I. The Synthesis of a Tetrapeptide," *J. Am. Chem. Soc.* 85:2149–2154 (1963).
Morse, J.H., "The Aggregation of γ–Myeloma Proteins," *J. Immunol.* 95(4):722–729 (1965).
Mumenthaler, M., et al., "Feasibility Study on Spray–Drying Protein Pharmaceuticals: Recombinant Human Growth Hormone and Tissue–Type Plasminogen Activator," *Pharmaceutical Research* 11(1):12–20 (Jan. 1994).

(List continued on next page.)

*Primary Examiner*—S. Mark Clardy
*Assistant Examiner*—Dameron Jones
*Attorney, Agent, or Firm*—Sterne, Kessler, Goldstein & Fox P.L.L.C.

[57] ABSTRACT

A lyophilized imaging agent formulation and methods for making same are disclosed, such formulations comprise a targeting molecule such as antibody or chemotactic peptide, a linker such as diethylenetriaminepentaacetic acid (DTPA) or succinimidyl 6-hydrazinium nicotinate hydrochloride (SHNH), drying protectant such as mannitol, maltose or tricine, and excipient such as polysorbate 80, in citrate buffer. The formulations of the invention are lyophilized and may be stored stably for extended periods of time. Following reconstitution with diluent, the formulations are administered to a subject for scintigraphic imaging or therapeutic use. Also contemplated is a kit comprising a two-vial system wherein a first vial comprises a lyophilized formulation of imaging agent in the form of a lyophilized cake, and a second vial comprises a pharmaceutically acceptable carrier or diluent.

35 Claims, 4 Drawing Sheets

OTHER PUBLICATIONS

Manning, M.C., et al., "Stability of Protein Pharmaceuticals," *Pharm. Res.* 6(11):903–918 (1989).

McCarthy, D., et al., "Instrinsically Stable IgG Aggregates," *J. Immunol. Methods* 41:63–74 (1981).

McCarthy, D., et al., "A Simple Procedure for Assessing the Stability of Heat–Aggregated IgG Preparations," *J. Immunol. Methods* 41:75–79 (1981).

Jøssang, T., et al., "Heat aggregation kinetics of human IgG," *J. Chem. Phys.* 82(1):574–589 (1985).

Lee, C.-l., et al., "A Solid–Phase Fluorescent Immunoassay for Human Prostatic Acid Phosphatase," *Cancer Research* 38:2871–2878 (1978).

Lougheed, W.D., et al., "Physical Stability of Insulin Formulations," *Diabetes* 32:424–432 (1983).

Hnatowich, D.J., et al., "The Preparation and Labeling of DTPA–Coupled Albumin," *Int. J. Appl. Radiat. Isot.* 33:327–332 (1982).

Humm, J.L., and Cobb, L.M., "Nonuniformity of Tumor Dose in Radioimmunotherapy," *J. Nucl. Med.* 31(1):75–83 (1990).

James, K., et al., "Structural Changes Occurring in 7S γ–Globulins," *Nature* 202:563–566 (1964).

Datz, F.L., et al., "The Efficacy of Indium–111–Polyclonal IgG for the Detection of Infection and Inflammation," *J. Nucl. Med.* 35(1):74–83 (Jan. 1994).

Everse, J., and Stolzenbach, F.E., "Lyophilization," *Methods in Enzymology XXII*:33–39 (1971).

Fischman, A.J., et al., "Imaging Focal Sites of Bacterial Infection in Rats with Indium–111–Labeled Chemotactic Peptide Analogs," *J. Nucl. Med.* 32(3):483–491 (1991).

Burgess, D.J., et al., "A Novel Method of Determination of Protein Stability," *Journal of Parenteral Science & Technology* 46(5):150–155 (1992).

Burnouf, T., et al., "A Highly Purified Factor VIII:c Concentrate Prepared from Cryoprecipitate by Ion–Exchange Chromatography," *Vox Sanguinis* 60:8–15 (1991).

Chawla, A.S., et al., "Aggregation of Insulin, Containing Surfactants, in Contact with Different Materials," *Diabetes* 34:420–424 (1985).

Abrams, M.J., et al., "Technetium–99m–Human Polyclonal IgG Radiolabeled via the Hydrazino Nicotinamide Derivative for Imaging Focal Sites of infection in Rats," *J. Nucl. Med.* 31(12):2022–2028 (1990).

Borrebaeck, C.A.K., "Strategy for the production of human monoclonal antibodies using in vitro activated B cells," *J. Immunol. Meth.* 123:157–165 (1989).

Bryant, R.L., and Barnett, J.B., "Adjuvant Properties of Retinol on IgE Production in Mice," *Int. Archs. Allergy Appl. Immunol.* 59:69–74 (1979).

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 6 amino acids
      (B) TYPE: amino acid
      (C) STRANDEDNESS: Not Relevant
      (D) TOPOLOGY: linear (ii) MOLECULE TYPE: peptide (ix) FEATURE:
      (A) NAME/KEY: Modified-site
      (B) LOCATION: 1
      (D) OTHER INFORMATION: /product= "Nle"
          /note= "1st residue is N-formylated"

(ix) FEATURE:
      (A) NAME/KEY: Modified-site
      (B) LOCATION: 4
      (D) OTHER INFORMATION: /product= "Nle"

(xi) SEQUENCE DESCRIPTION: SEQ ID NO:1:

Xaa Leu Phe Xaa Tyr Lys
1            5

(2) INFORMATION FOR SEQ ID NO:2:

(i) SEQUENCE CHARACTERISTICS:
        (A) LENGTH: 4 amino acids
        (B) TYPE: amino acid
        (C) STRANDEDNESS: Not Relevant
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "1st residue is complexed
            with an isobutyloxycarbonyl (iBoc) group"

(xi) SEQUENCE DESCRIPTION: SEQ ID NO:2:

Met Leu Phe Lys
1

(2) INFORMATION FOR SEQ ID NO:3:

(i) SEQUENCE CHARACTERISTICS:
        (A) LENGTH: 4 amino acids
        (B) TYPE: amino acid
        (C) STRANDEDNESS: Not Relevant
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "Nle"
            /note= "1st residue is N-formylated"

(xi) SEQUENCE DESCRIPTION: SEQ ID NO:3:

Xaa Leu Phe Lys
1

(2) INFORMATION FOR SEQ ID NO:4:

(i) SEQUENCE CHARACTERISTICS:
        (A) LENGTH: 4 amino acids
        (B) TYPE: amino acid
        (C) STRANDEDNESS: Not Relevant
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "N-formylmethionine"
            /label= fMet (xi) SEQUENCE DESCRIPTION: SEQ ID NO:4:

Met Leu Phe Lys
1

(2) INFORMATION FOR SEQ ID NO:5:

(i) SEQUENCE CHARACTERISTICS:
        (A) LENGTH: 4 amino acids
        (B) TYPE: amino acid
        (C) STRANDEDNESS: Not Relevant
        (D) TOPOLOGY: linear (ii) MOLECULE TYPE: peptide (ix) FEATURE:

```
        (A) NAME/KEY: Modified-site
        (B) LOCATION: 1
        (D) OTHER INFORMATION: /product= "N-formylmethionine"
            /label= fMet (ix) FEATURE:
        (A) NAME/KEY: Modified-site
        (B) LOCATION: 4
        (D) OTHER INFORMATION: /product= "D-lysine"
            /note= "4th residue is (D)-amino acid"

(xi) SEQUENCE DESCRIPTION: SEQ ID NO:5:

Met Leu Phe Lys
```

LYOPHILIZED IMAGING AGENT FORMULATION COMPRISING A CHEMOTACTIC PEPTIDE

This is a division of U.S. Utility patent application Ser. No. 08/271,818, filed Jul. 7, 1994, now abandoned, the contents of which are incorporated herein by reference.

BACKGROUND OF THE INVENTION

One of the preeminent concerns in the field of protein, peptide and antibody production for commercial supply is formulation of a stable, bioactive product that can withstand transport from manufacturing site to storage, shipping and delivery to the end user. Prior formulations have proven unstable in varying environments of temperature and light exposure. Liquid formulations can be particularly unstable, and prior immunoglobulin solutions, for example, have developed particles upon storage rendering them unsuitable for intravenous use. Such precipitation requires the additional step of filtration before use. In addition, such liquid formulations have demonstrated loss of bioactivity, increased aggregation into liver as detected by biodistribution studies, and, in the instance of antibody for imaging studies, loss of radionuclide labeling efficiency.

Another problem with antibody supply has been the presentation of the imaging agent in a multiple-vial system. For example, prior imaging agent formulations have consisted of two vials for $^{111}$In chloride labeling prior to imaging. In such formulation, the first vial contained imaging agent (DTPA-IgG) in phosphate buffered saline, pH 7.5, whereas the second vial contained 0.25M sodium citrate buffer, pH 5.5.

Among the further disadvantages of this system were the need for physical manipulation (e.g., transfer of solution from the primary to the secondary vial).

More specifically, concerning particle formation, aggregates of IgG have been reported to fix complement and bind macrophages in a way similar to antigen-antibody complexes (T. Jossang, J. Feder, and E. Rosenqvist. Heat Aggregation Kinetics of Hyman IgG. *J. Chem Phys.* 82:574–589 (1985); J. Tschopp. Kinetics of Activation of the First Component of Complement (ci) by IgG Oligomers. *Mol Immunol.* 19:651–657 (1982)). For this reason, a great number of studies on IgG aggregation and degradation have been reported in the literature (T. Jossang, J. Feder, and E. Rosenqvist. Heat Aggregation Kinetics of Hyman IgG. *J. Chem Phys.* 82:574–589 (1985); J. Tschopp. Kinetics of Activation of the First Component of Complement (ci) by IgG Oligomers. *Mol Immunol.* 19:651–657 (1982); H. N. Eisen. *Immunology: An Introduction to Molecular and Cellular Principles of the Immune Responses.* 2nd ed. Harper & Row, Philadelphia, 1980; K. James, C. S. Henney, and D. R. Stanworth. Structural Changes Occurring in 7S γ-globulins. *Nature.* 202:563–566 (1964); J. H. Morse. The Aggregation of γ-myeloma Proteins. *J. Immun.* 95:722–729 (1965); I. Oreskes, and D. Mandel. Size Fractionation of Thermal Aggregates of Immunoglobulin G. *Anal Biochem.* 134:199–204 (1983); V. P. Zav'yalov, G. V. Troitsky, A. P. Demchenko, and I. V. Generalov. Temperature and pH Dependent Changes of Immunoglobulin G Structure. *Biochim Biophys Acta.* 386:155–167 (1975); D. McCarthy, D. H. Goddard, P. H. Embling, and E. J. Holborow. A Simple Procedure for Assessing the Stability the Heat-aggregated IgG Preparations. *J. Immunol Methods.* 41:75–59 (1981); D. McCarthy, D. H. Goddard, B. K. Pell, and E. J. Holborow. Intrinsically Stable IgG Aggregates. *J Immunol Methods.* 41:63–74 (1981); E. Rosenqvist, T. Jossang, and J. Feder. Thermal Properties of Human IgG. *Mol Immun.* 24:495–501 (1987)). Thermal stress of IgG in solution is the most commonly reported means of inducing this aggregation. This thermally induced IgG aggregation has been reported to be irreversible (T. Jossang, J. Feder, and E. Rosenqvist. Heat Aggregation Kinetics of Hyman IgG. *J. Chem Phys.* 82:574–589 (1985); E. Rosenqvist, T. Jossang, and J. Feder. Thermal Properties of Human IgG. *Mo/Immun.* 24:495–501 (1987)) and a function of both time and temperature (I. Oreskes, and D. Mandel. Size Fractionation of Thermal Aggregates of Immunoglobulin G. *Anal Biochem.* 134:199–204 (1983)), with sharp increase in rate of aggregation occurring at 63° C. (D. McCarthy, D. H. Goddard, B. K. Pell, and E. J. Holborow. Intrinsically Stable IgG Aggregates. *J Immunol Methods.* 41:63–74 (1981)). Both soluble and insoluble aggregates have been reported depending on the sample treatment conditions (J. H. Morse. The Aggregation of γ-myeloma Proteins. *J. Immun.* 95:722–729 (1965); I. Oreskes, and D. Mandel. Size Fractionation of Thermal Aggregates of Immunoglobulin G. *Anal Biochem.* 134:199–204 (1983)) and the preparation (D. McCarthy, D. H. Goddard, P. H. Embling, and E. J. Holborow. A Simple Procedure for Assessing the Stability the Heat-aggregated IgG Preparations. *J. Immunol Methods.* 41:75–59 (1981)).

Aggregation phenomena are of potential concern in the preparation of antibody-based pharmaceuticals (M. C. Manning, K. Patel, and R. T. Borchardt. Stability of Protein Pharmaceuticals. *Pharm. Res.* 6:903–918 (1989)). One such preparation, an imaging agent discussed herein, consists of human polyclonal IgG conjugated to DTPA diethylenetriamine pentaacetic anhydride. As disclosed in the instant invention, subsequent to conjugation the imaging agent product is formulated in a citrate buffer containing maltose, and lyophilized. DTPA-IgG when labeled with $^{111}$In, and administered to patients, localizes at sites of infection and/or inflammation. Six to 72 hours post-injection these sites can be detected by subjecting the patient to gamma-scintigraphy (R. H. Rubin, A. J. Fischman, R. J. Callahan, B. Khaw, F. Keech, M. Ahmad, R. Wilkinson, and H. W. Strauss. $^{111}$In-labeled Nonspecific Immunoglobulin Scanning in the Detection of Focal Infection. *N Engl J Med.* 321:935–940 (1989); W. Oyen, R. Claessens, J. Van Horn et al. Scintigraphic Detection of bone and Joint Infections with Indium-111-labeled Non-specific Polyclonal Human Immunoglobulin G. *J Nucl Med.* 31:403–412 (1990)).

The major pathway of degradation for reconstituted DTPA exposed to both light and heat and to lyophilized DTPA-IgG exposed to light is aggregation and precipitation, similar to findings reported for intact human IgG ((T. Jossang, J. Feder, and E. Rosenqvist. Heat Aggregation Kinetics of Hyman IgG. *J. Chem Phys.* 82:574–589 (1985); J. H. Morse. The Aggregation of γ-myeloma Proteins. *J. Immun.* 95:722–729 (1965); I. Oreskes, and D. Mandel. Size Fractionation of Thermal Aggregates of Immunoglobulin G. *Anal Biochem.* 134:199–204 (1983); V. P. Zav'yalov, G. V. Troitsky, A. P. Demchenko, and I. V. Generalov. Temperature and pH Dependent Changes of Immunoglobulin G Structure. *Biochim Biophys Acta.* 386:155–167 (1975); D. McCarthy, D. H. Goddard, P. H. Embling, and E. J. Holborow. A Simple Procedure for Assessing the Stability the Heat-aggregated IgG Preparations. *J. Immunol Methods.* 41:75–59 (1981); D. McCarthy, D. H. Goddard, B. K. Pell, and E. J. Holborow. Intrinsically Stable IgG Aggregates. *J Immunol Methods.* 41:63–74 (1981); E. Rosenqvist, T. Jossang, and J. Feder. Thermal Properties of Human IgG. *Mol Immun.* 24:495–501 (1987)). In particular regarding DTPA, DTPA itself is hydrolyzed rapidly and thus will not bind to $^{111}$InCl (Hnatowich D J, Layne W W, Childs R L, The preparation and labeling of DTPA-coupled albumin. Int. J. Appl. Radiat. Isol. 1982, 33:327–332)). In contrast, lyophilized DTPA IgG subjected to thermal stress showed no tendency to precipitate and only slight evidence of aggregation. The principle change observed under these conditions was a gradual increase in size of the IgG monomer, however, shifts in retention time and total protein were found (Hekman, C et al., in press). This increase in size, too small to be attributed to the formation of IgG dimers or trimers, was a function of the time the sample was subjected to stress and to the moisture content of the sample. Data suggest that this increase in size was due to the covalent attachment of the excipient maltose to the IgG by a non-enzymatic glucosylation reaction.

The instant invention provides a solution to both the problems of imaging agent stability and presentation, by providing for a (1) lyophilized formulation, (2) in a single vial. The liquid formulation is lyophilized, or freeze-dried, by first exposing opened vials of the formulation to step-wise temperature decrease to freezing, in vacuum, to effect sublimation of the water from the sample. The resulting product is a powder or cake which upon sealing with a stopper and seal can be stored for extended periods and shipped to the end user while maintaining activity and stability. The cake is reconstituted just prior to time of use by rehydration of the cake with an aqueous solution such as water for injection, buffer or other diluent suitable for pharmaceutical use. Following reconstitution and gentle admixture, and labeling with radionuclide, the solution is ready to be administered to the subject.

In particular, the invention contemplates use of an excipient and a drying protectant in admixture with a targeting molecule (e.g. antibody or chemotactic peptide) at a selected range of pH, which composition is lyophilized. The excipient prevents the precipitation of the antibody solution once reconstituted, thus enhancing safety of the composition for in vivo use. The selected pH range employed results in an increase in labeling efficiency. Stability of the lyophilized formulation is greater than that of the corresponding liquid formulation. Alternatively, the formulation may be frozen (at about −40° C. to about −70° C.), however, freeze-rethaw cycles can adversely affect the protein.

Throughout this disclosure, various publications, patents and patent applications are referenced. The disclosures of these publications, patents and applications in their entireties are hereby incorporated by reference into this disclosure in order to more fully describe the state of the art as known to those skilled therein as of the date of the invention described and claimed herein.

SUMMARY OF THE INVENTION

The instant invention relates to an imaging agent composition comprising a targeting molecule, a linker, and a drying-protectant, wherein the composition has a pH of about 3.0–6.5. The imaging agent may also comprise an excipient. The targeting molecule may comprise human immune globulin such as for example IgG, or may comprise a chemotactic peptide. The linker may be for example diethylenetriaminepentaacetic acid (DTPA) or succinimidyl 6-hydrazinium nicotinate hydrochloride (SHNH). The drying protectant is preferably a saccharide, for example maltose or mannitol, or in the case of hydrazide linkers, tricine. The drying protectant may be present in the final lyophilized composition in a weight percent to targeting molecule in the range of about 500% to about 2000%. When SHNH linker is employed, the drying protectant is present in the final lyophilized composition in a weight ratio of targeting molecule to drying protectant in the range of about 1:5 to 1:500, more preferably about 1:20 to 1:100. The excipient may be a polymer, for example polysorbate 80 (TWEEN 80). Preferably the composition is formulated in a citrate buffer. The linker-derivatized targeting molecule is chelated to a radionuclide such as for example $^{111}$In or $^{99m}$Tc for scintigraphic imaging, or alternatively for therapeutic use, employing therapeutic radionuclides.

Also contemplated is a lyophilized formulation of imaging agent, and a kit comprising a two-vial system wherein a first vial comprises a lyophilized formulation of imaging agent in the form of a lyophilized cake, and a second vial comprises a pharmaceutically acceptable carrier or diluent, for example, sterile water or sterile sodium chloride buffer.

Methods for preparing aqueous imaging agent compositions, and lyophilizing and reconstituting same are also disclosed.

BRIEF DESCRIPTION OF THE DRAWING

FIG. 2 is a schematic diagram of manufacture of lyophilized DTPA complexed to IgG ("DTPA-IgG").

DETAILED DESCRIPTION OF THE INVENTION

Figure 1:
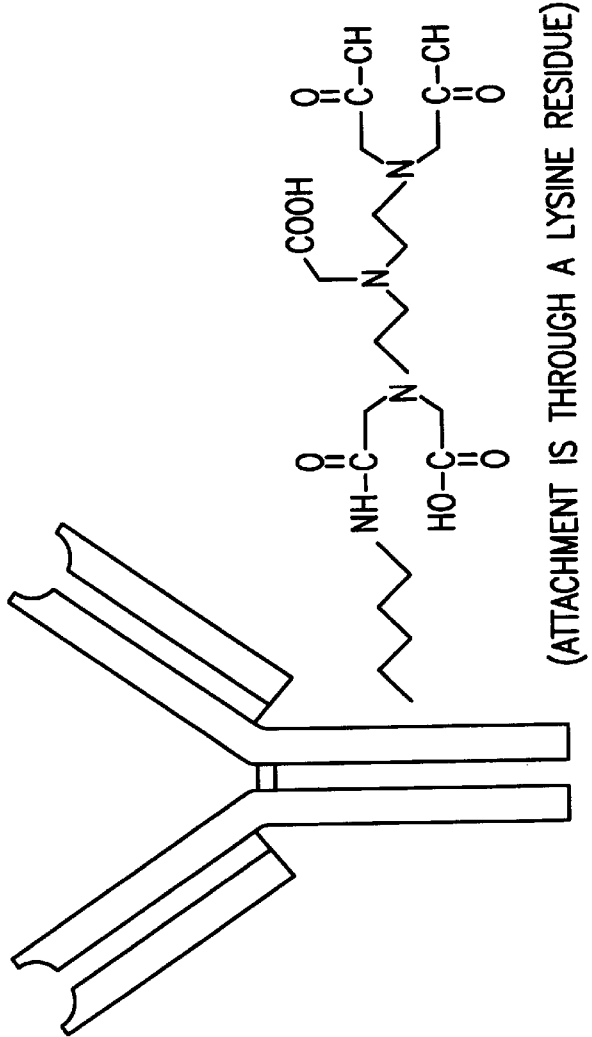
FIG. 1 is a structural formula of a conjugate of human immune serum globulin and diethylenetriaminepentaacetic acid ("DTPA-IgG").
Figure 2A:
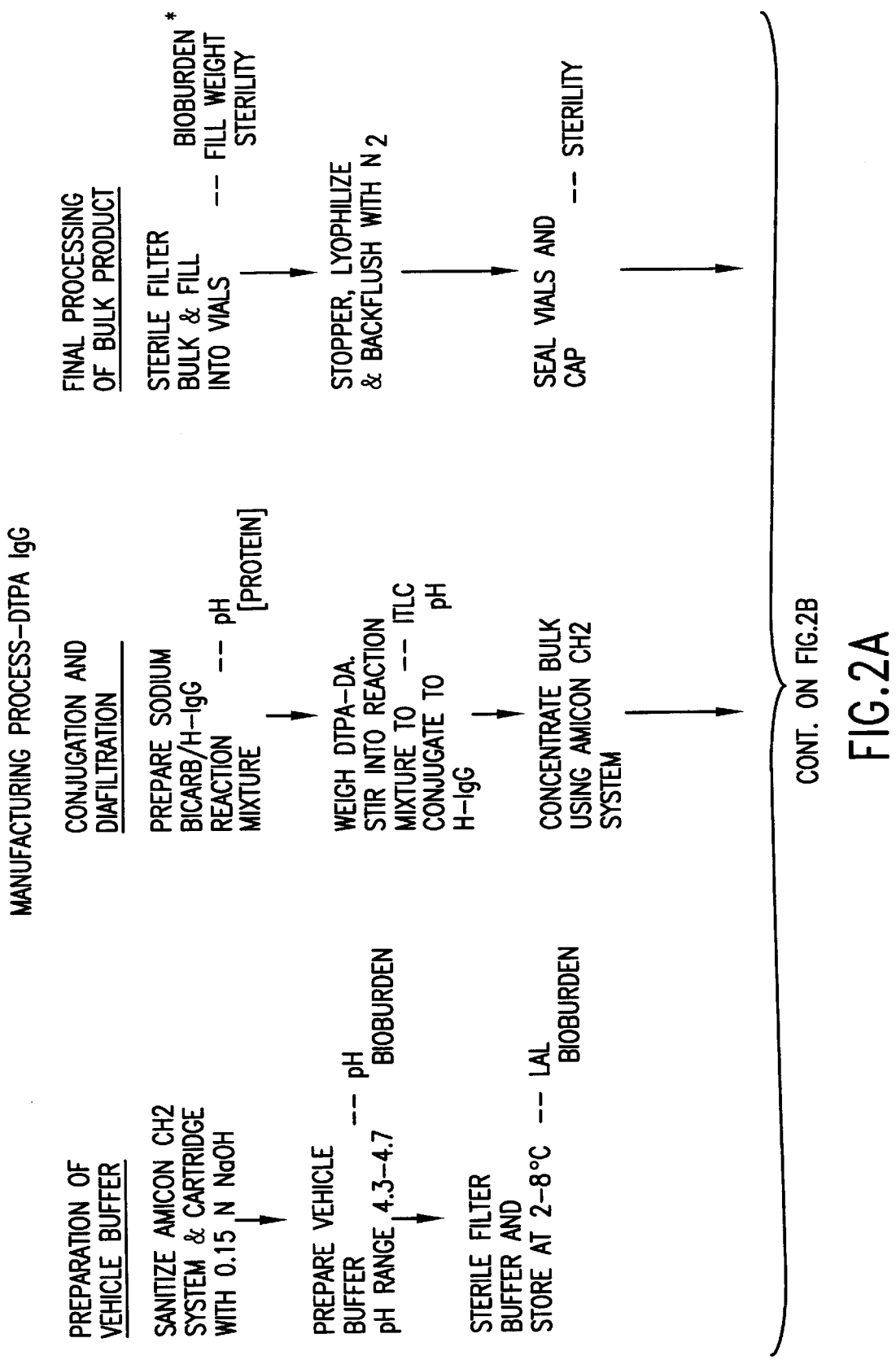
FIGS. 2A and 2B are a schematic diagram of manufacture of lyophilized DTPA complexed to lgG ("DTPA-lgG").
Figure 2B:
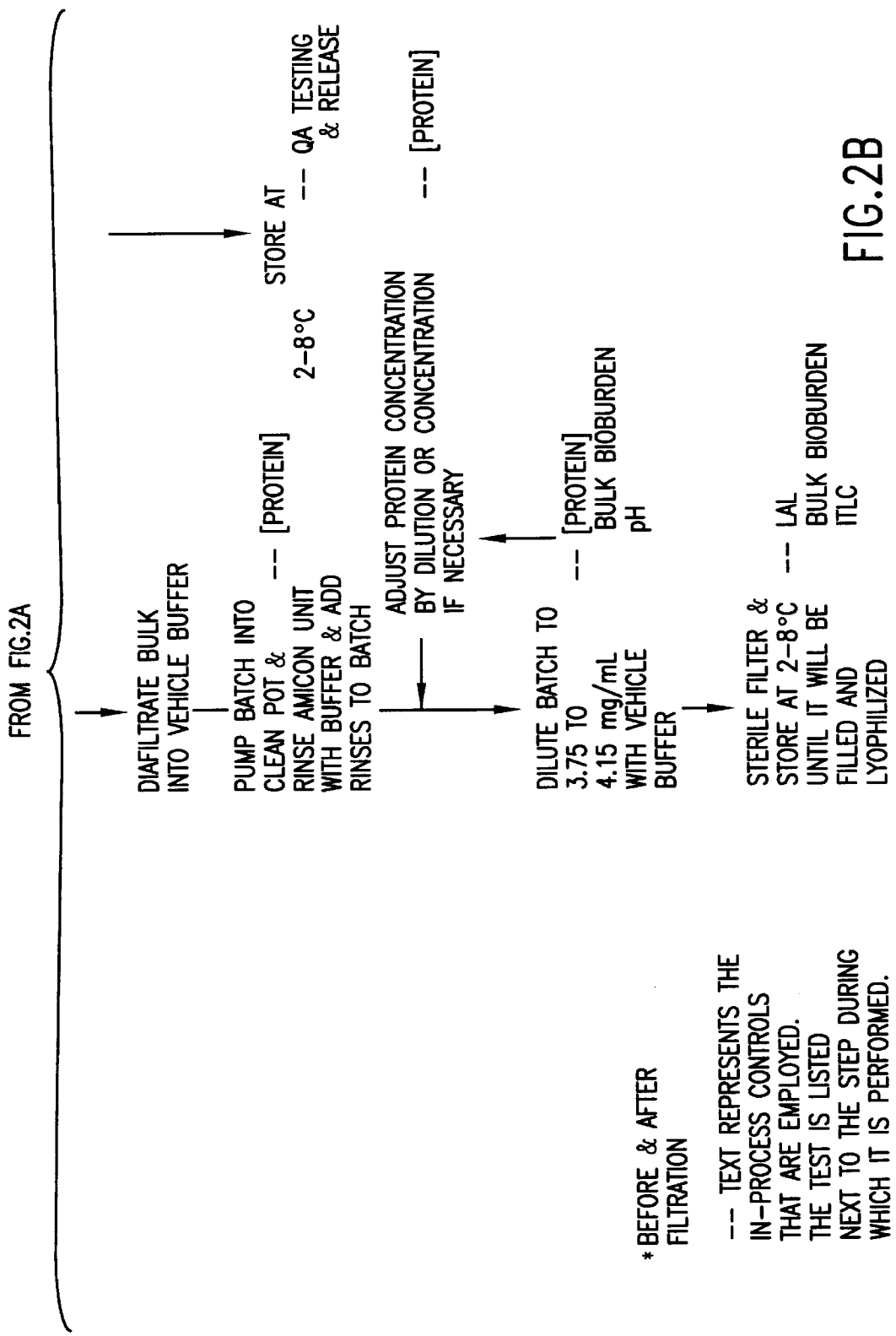
Figure 3:
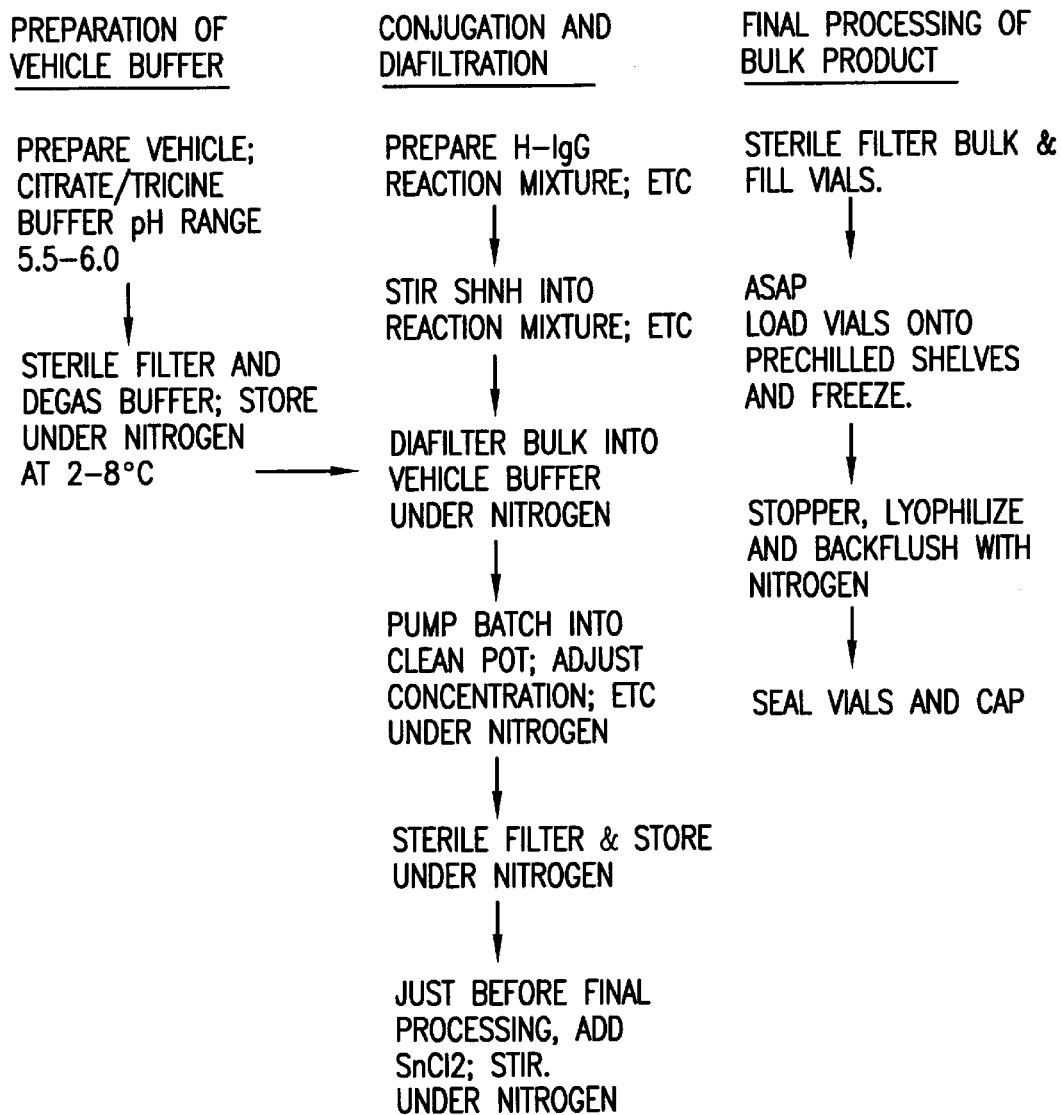
FIG. 3 is a schematic diagram of manufacture of lyophilized succinimidyl 6-hydrazinium nicotinate hydrochloride complexed to IgG ("SHNH-IgG").

The lyophilized imaging agent compositions of the present invention have a low water content, preferably from about 0%–5% water, more preferably about 2.5% water by weight. The presence of water in the lyophilized compositions tends to decrease the biological activity of the imaging agents at more extreme levels and may reduce the aesthetic appearance of the lyophilized cake or plug at levels greater than about 3–5% by weight. Biological activity may be measured in recognized bioassays, such as the biodistribution focal infection assay, referenced herein in Example 7. Additionally, stability of the imaging agent may be measured by any suitable HPLC method.

Imaging agent compositions of the instant invention comprise a targeting molecule, a drying protectant and preferably an excipient, and are formulated in an aqueous solution of low pH, preferably around about pH 3.0 to about 6.5, which pH range is dependent upon the linker employed. The targeting molecule is an immunologically reactive molecule, or a molecule capable of differential localization in human subjects as a function of metabolic and/or physico-chemical characteristics of specific tissues. For example, targeting molecules contemplated in the instant invention include antibodies, for example human immune globulin or IgG, and fragments thereof. The antibodies may be monoclonal or polyclonal, and isolated or synthesized using a variety of methods including recombinant DNA techniques. The antibody may be human or non-human antibody (murine), and additionally may be humanized murine antibody. Also contemplated as targeting molecules in this invention are chemotactic peptides described in copending U.S. Ser. No.

140,000, filed Oct. 22, 1993, incorporated by reference herein, which include but are not limited to, N-formyl-Nle-Leu-Phe-Nle-Tyr-Lys (SEQ ID NO: 1), iBoc-MLFK (SEQ ID NO: 2), and N-formyl-Nle-Leu-Phe-Lys (SEQ ID NO: 3), among others.

The drying protectant for use in the present invention can be any of the pharmaceutically acceptable essentially inert solid materials typically used for lyophilization in the formulation art. As used herein, the term "drying protectant" means a water soluble, solid particulate diluent used for facilitating lyophilization by increasing the bulk, or solid material, present in the final lyophilized composition. Thus, the drying protectant provides mechanical integrity to the lyophilized cake. The drying protectant should be non-toxic, it should not decrease the bioactivity of the imaging agent and it should have no specific pharmacological action in the amount used. Such drying protectants include simple sugars, such as monosaccharides, including glucose, dextrose, and maltose and the sugar alcohol mannitol; disaccharides, such as sucrose and lactose; polysaccharides such as dextran; amino acids such as glycine and tris(hydroxymethyl) methylglycine ("tricine"), and alanine; short chain ($C_3$–$C_6$) tricarboxylic and dicarboxylic acids, such as citric acid, glutamic acid and tartaric acid; and certain inorganic salts, such as the sodium or potassium phosphates. In a preferred embodiment, the drying protectant is maltose, mannitol, glycine, glutamic acid, or tricine, which can be used either together or in combination. When tricine is used, it has been determined that such drying protectant also allows for faster labeling and higher specific activity. In any final reconstituted DTPA-IgG solution of the present invention, the concentration of drying protectant should be between about 0.1 and about 10.0% (w/v). The ratio of the weight of targeting molecule to the weight of drying protectant used in the compositions of the present invention employing the DTPA linker should in general be within the range of about 0.00001 to about 0.5%, (w/w) but in any case is only limited by concentrations that will interfere with the bioactivity of the imaging agent. The ratio of the weight of targeting molecule to the weight of drying protectant used in the compositions of the present invention employing the SHNH linker in conjunction with antibody should in general be within the range of about 0.001–2.8% (w/w), more preferable about 0.5–2.5% (w/w). The ratio of the weight of targeting molecule to the weight of drying protectant used in the compositions of the present invention employing the SHNH linker in conjunction with chemotactic peptide will in general be from about 1:5 to 1:500.

Since antibodies such as IgG tend not to crystallize well, or not at all, and do not pack well by themselves in lyophilized form, the drying protectant enhances the packing of the lyophilized growth factor into a solid "cake". In general, the amount of drying protectant is limited only by osmolarity for patient comfort upon injection. For example, common sugars are isoosmolar at a concentration of about 5%, however, glycine is isoosmolar at 2–2.5%.

In general, the final lyophilized reconstituted solution should contain sufficient drying protectant, excipient and sodium chloride to adequately prevent aggregation, yet provide a near-isotonic solution (250–350 mOsm/L) for patient comfort upon injection and be below the critical micelle concentration of the excipient.

All subclasses of IgG can be used as antibody targeting molecule e.g. $IgG_1$, $G_2$, G2a, G2b and $G_3$. The targeting molecule (e.g., antibody or fragment thereof or chemotactic peptide) is derivatized so that it binds with a radioisotope, such as Technetium-99m ($^{99m}Tc$) or Indium-111 ($^{111}In$). The targeting molecule can be derivatized either by changing its native state so that a radioisotope can be bound directly to it, or with a linker such as diethylenetriamine pentacetic acid (DTPA) or a hydrazine linking agent such as succinimidyl 6-hydrazinium nicotinate hydrochloride (SHNH) or succinimidyl 2-(2-propenylhydrazone) nicotinate (SPNH). The derivatized targeting molecule can be used as a radiopharmaceutical due to the derivatized molecule's ability to bind a radioactive heavy metal ($^{111}In$ or $^{99m}Tc$) to the targeting molecule protein, forming a protein-radioisotope complex, or in the case of a linker, a protein-linker-radioisotope complex. The radiolabeled targeting molecule can then be used in radioimaging, for example, in in vivo diagnostic imaging of tumors or disease states, for example, inflammation or infection.

For the purposes herein, the defined term "imaging agent" comprises a conjugate formed between "targeting molecule", such as monoclonal or polyclonal human immune globulin (IgG) or chemotactic peptide, and a "linker", for example, DTPA or SHNH, and in which other components may be present such as for example drying protectant and excipient. The structural formula of DTPA-IgG is depicted in FIG. 1.

Subsequent to labeling with a radionuclide, such as $^{111}In$ or $^{99m}Tc$, imaging agent (e.g., DTPA-IgG) is useful for detecting focal sites of infection and inflammation (Rubin et al., U.S. Pat. No. 4,926,869, and Rubin et al., N. Engl. J. Med., (1989) 321:935–940).

Preferred excipients in the instant invention include vinyl polymers, polyoxyethylene-polyoxypropylene polymers or co-polymers (PLURONICS), polysaccharides, proteins, poly(ethyleneoxide), and acrylamide polymers and derivatives or salts thereof. It is understood that poly (ethyleneoxide) includes polyethylene glycol. The vinyl polymers useful in the present invention may be selected from the group consisting of polyacrylic acid, polymethacrylic acid, polyvinyl pyrrolidone and polyvinyl alcohol. The polysaccharides useful in the present invention may be selected from the group consisting of cellulose or cellulose derivatives, glycosaminoglycans, agar, pectin, alginic acid, dextran, starch and chitosan. The glycosaminoglycans may be selected from the group consisting of hyaluronic acid, chondroitin, and related molecules. The proteins useful in the present invention may be selected form the group consisting of collagen, gelatin and fibronectin.

The cellulose derivatives may include alkyl cellulose and hydroxyalkyl cellulose, for example, methyl cellulose, hydroxyethyl cellulose, carboxymethyl cellulose, hydroxypropylmethyl cellulose and hydroxypropyl cellulose.

Especially preferred are propylene glycol, polyethylene glycol, and polysorbate 80 (TWEEN).

The excipients are employed at a concentration range of about 0.04 mg to 40 mg excipient per 4.0 mg targeting molecule, or about 1000% by weight. Particularly preferred is polysorbate 80, which is employed at a concentration in the lyophilized formulation of about 0.4 mg polysorbate 80 per 4.0 mg targeting molecule, or 10% by weight. In the final reconstituted solution, the concentration of polysorbate 80 is between about 0.001 percent and 0.1 per cent w/v, and is most preferably 0.01% by volume. The amounts of excipient recited in this paragraph are specific for DTPA-IgG, however, it is contemplated that said amounts would be applicable to other formulations of linker-targeting molecule, for example, SHNH-IgG and SHNH-chemotactic peptide. In general, the amounts of excipient would be about the same for all linker-targeting molecules that are administered in about the same dosage (64 mg/mL), but excipient should be present in amounts below the critical micelle concentration.

A preferred embodiment of the invention is a formulation for lyophilization of targeting molecule comprising IgG, that contains a buffer having a low pH (between about 3.0 and 6.5), a drying protectant and an excipient. Preferred buffers include sodium acetate, phosphate, and citrate buffers, most preferably citrate buffer at about pH 3.0–6.5. Where the imaging agent is DTPA-targeting molecule, the pH will be in the range of 3.0–6.0, most preferably about pH 4.5. Where the imaging agent is SHNH-targeting molecule, the pH will be in the range of 5.0–6.5, more preferably about 5.2–5.5. Preferred drying protectants are those referenced hereinabove, preferably the monosaccharides, most preferably, maltose in the case of DTPA-targeting molecule, and most preferably tricine in the case of SHNH-targeting molecule. In the preferred lyophilized DTPA-IgG imaging agent formulation of the instant invention, the drying protectant is present in about 50 mg drying protectant (i.e. maltose) per 4 mg IgG, or at about 1250% by weight. In the final reconstituted solution, the concentration of maltose is most preferably between about 0.1 and 6% (w/v).

Where the radioisotope to be employed is $^{111}$In, imaging agent formulation is preferably initially formulated at 4 mg/ml DTPA-IgG in 80 mM citrate buffer, pH 4.3–4.7, containing 5% maltose and 0.04% polysorbate 80. IgG is conjugated to the linker diethylenetriamine pentacetic acid (DTPA). Conjugation is by the Hnatowich procedure with DTPA bicyclic anhydride (DTPA-DA, available from Pierce Chemical Co., (Rockford, Ill.) (Hnatowich D J, Layne W W, Childs R L, The preparation and labeling of DTPA-coupled albumin. Int. J. Appl. Radiat. Isol. 1982, 33:327–332). One-half ml (0.5 mL) of this imaging agent formulation is filled into 3 mL vials and lyophilized. After reconstitution with 2 ml of 0.9% saline, the imaging agent formulation is 1 mg/ml DTPA-IgG in 20 mM citrate buffer, pH 4.3–4.7, containing 1.25% maltose 0.01% polysorbate 80, and 0.9% sodium chloride.

There are many different labels and methods of labeling known to those skilled in the art. Examples of the types of labels that can be used in the present invention include radioactive isotopes, paramagnetic isotopes, and compounds that can be imaged by positron emission tomography (PET). Those skilled in the art will know of other suitable labels for binding to the targeting molecules used in the invention, or will be able to ascertain such using routine experimentation. Furthermore, the binding of these labels to the targeting molecules can be done using standard techniques common to those skilled in the art.

For diagnostic in vivo imaging, the type of detection instrument available is a major factor in selecting a given radionuclide. The radionuclide chosen must have a type of decay that is detectable by a given type of instrument. In general, any conventional method for visualizing diagnostic imaging can be utilized in accordance with this invention.

Another important factor in selecting a radionuclide for in vivo diagnosis is that its half-life be long enough that it is still detectable at the time of maximum uptake by the target tissue, but short enough that deleterious radiation of the host is minimized. In one preferred embodiment, a radionuclide used for in vivo imaging does not emit particles, but produces a large number of photons in a 140–200 keV range, which may be readily detected by conventional gamma cameras.

Examples of metallic ions (radioisotopes) that can be bound to imaging agents of the instant invention are $^{99m}$Tc, $^{123}$I, $^{131}$I, $^{97}$Ru, $^{67}$Cu, $^{67}$Ga, $^{125}$I, $^{68}$Ga, $^{72}$As, $^{89}$Zr, and $^{201}$Tl. $^{99m}$Tc and $^{111}$In are preferred.

Although numerous techniques have been used for $^{99m}$Tc labeling of imaging agents, the hydrazino nicotinamide group (HYNIC) has been especially promising. The active succinimidyl ester of hydrazinonicotinic acid (SHNH) has been successfully used to derivatize the epsilon amino groups of lysine residues in proteins. Incubation of these conjugates with simple complexes possessing the Tc(V) oxo core such as $^{99m}$Tc-glucoheptonate results in quantitative labeling (Abrams, M. J., et al., J. Nucl. Med. 31:2022–2028 (1990)), pending U.S. Ser. No. 140,000, filed Oct. 22, 1993.

The currently preferred method for labeling with $^{99m}$Tc is the reduction of pertechnetate ion in the presence of a chelating precursor to form the labile $^{99m}$Tc-precursor complex, which, in turn, reacts with the metal binding group of a bifunctionally modified chemotactic peptide to form a $^{99m}$Tc-chemotactic peptide conjugate. As stated above, $^{99m}$Tc-glucoheptonate can be used to radiolabel proteins that have been modified with SHNH groups (Schwartz, D. A., et al., Bioconjugate Chem. 2:333–336 (1991)). However, this requires a sixty minute incubation and specific activities greater than 25 mCi/mg to achieve radiolabelling yields greater than 90%. The polyhydroxyamino acid tricine can be used as a more efficient and facile labelling precursor for $^{99m}$Tc labelling of SHNH modified polypeptides and proteins as disclosed in pending U.S. Ser. No. 140,000, filed Oct. 22, 1993.

Of particular utility in the formation of linker-IgG conjugates is the use of an IgG-linker conjugate in conjunction with stannous ion and tricine, which method is disclosed in pending U.S. Ser. No. 140,000, filed Oct. 22, 1993. Tricine, (tris(hydroxymethyl)methylglycine), and analogues thereof, can be formulated in aqueous solutions, pH 6–8, with stannous chloride reducing agent for the spontaneous formation of $^{99m}$Tc precursors. Analysis for the formation of "Tc-tricine" is performed on ITLC-SG strips, similar to $^{99m}$Tc-glucoheptonate analysis, using saline for the quantitation of TcSn colloid at the origin and methylethylketone for the quantitation of pertechnetate at the solvent front. Solutions of "Tc-tricine" (36 mg/ml precursor, 50 µg/ml stannous chloride, pH 6.0), under similar conditions to $^{99m}$Tc-glucoheptonate, radiolabelled SHNH modified IgG to greater than 90% in minutes at room temperature. Additionally, solutions of "Tc-tricine" can achieve >90% radiolabelling of IgG-SHNH at specific activities greater than 150 mCi/mg protein as compared to Tc-glucoheptonate pending (U.S. Ser. No. 140,000, filed Oct. 22, 1993).

In a preferred embodiment of the invention, imaging agent, for example DTPA-IgG, in a concentration of 1.0 mg/mL, has the following formulation:

saline (0.9%)
maltose (1.25%)
polysorbate 80 (0.01%) (TWEEN)
citrate buffer (20 mM)
pH 4.5

Said formulation in solution or following lyophilization retains activity as measured by $^{111}$In-chloride labeling efficiency, referenced herein in Example 7, and more particularly, by target:background ratio as measured in biodistribution assay, referenced herein in Example 7.

We have found that use of the excipient polysorbate 80 in an aqueous formulation of DTPA-IgG imaging agent having pH of 4.5 increases the labeling efficiency and decreases aggregation and particulate formation in the reconstituted formulation, as compared to formulations of DTPA-IgG imaging agent without those characteristics of excipient and pH (See Examples 12 and 13, and Tables referenced therein).

In another embodiment, the imaging agent, for example SHNH-IgG, in a concentration of 1.0 mg/mL, has the following formulation:

saline (0.9%)

maltose (1.25%)

polysorbate 80 (0.01%) (TWEEN)

citrate buffer (20 mM)

pH 5.2

The formulation may additionally comprise tricine, $SnCl_2$, and glycine or mannitol may be substituted for maltose. Alternatively, tricine may be substituted for mannitol and maltose.

In yet another embodiment of the invention, imaging agent, for example SHNH-chemotactic peptide, in a concentration of 1.0 mg/mL, has the following formulation:

saline (0.9%)

maltose (1.25%)

polysorbate 80 (0.01%) (TWEEN)

citrate buffer (20 mM)

pH 5.2

This formulation may additionally contain tricine and $SnCl_2$, and glycine or mannitol may be substituted for maltose. Alternatively, tricine may substitute for maltose and mannitol.

When $SnCl_2$ is employed in the formulations, dissolved IgG is mixed with stannous ion, preferably chloride, and with a stabilizer for the stannous ions. Stannous ion is readily available as its dihydrate, or it can be generated in s from tin metal, e.g., foil, granules, powder, turnings and the like, by contact with aqueous acid, e.g., HCl. It is usually added in the form of $SnCl_2$, advantageously in a solution that is also about 0.01 N in HCl, in a ratio of about 2.5–150$\mu$g Sn/mg protein, preferably about 50 $\mu$g Sn/mg of fragment, allowing for potential decomposition or oxidation of Sn during the lyophilization cycle. Advantageously, the stannous ion solution is prepared by dissolving $SnCl_2.2H_2O$ in 6N HCl and diluting the resultant solution with sterile $H_2O$ that has been purged with argon.

A stabilizing agent for the stannous ion is advantageously present in the solution. It is known that ascorbate can improve specific loading of a chelator with reduced pertechnetate and minimize formation of $TcO_2$, when the reducing agent is stannous ion. Other polycarboxylic acids, e.g., tartrate, citrate, phthalate, iminodiacetate, ethylenediaminetetraacetic acid (EDTA), diethylenetriaminepentaacetic acid (DTPA) and tricine, and the like, can also be used. Although polycarboxylic acids are mentioned, by way of illustration, any of a variety of anionic and/or hydroxylic oxygen-containing species could serve this function, e.g., salicylates, acetylacetonates, hydroxyacids, catechols, glycols and other polyols, e.g., glucoheptonate, and the like. Preferred such stabilizers are ascorbate, citrate and tartrate, more preferably tartrate.

While the precise role of such agents is not known, it appears that they chelate stannous ion and may prevent adventitious reactions and/or promote reduction of $^{99m}Tc$ by stabilization of stannous ions, and they may also chelate—and thereby stabilize—certain oxidation states of reduced pertechnetate, thereby serving as transchelating agents for the transfer of these technetium ions to the presumably more stable chelation with one or more thiol groups and other nearby ligands on the protein. Such agents will be referred to as "stabilizers" herein. The molar ratio of stabilizer to stannous ion is about 30:1–40:1.

A solution of stabilizer, e.g., NaK tartrate, advantageously at a concentration of about 0.1 M, in buffer, preferably sodium acetate at a pH of about 5.5, is prepared with sterile $H_2O$ purged with argon. One volume of the $SnCl_2$ solution is mixed with enough of the stabilizer solution to provide a 30–40 molar excess, relative to the stannous ion, and resultant solution is sterile filtered and purged with argon.

The sterile, stabilized $SnCl_2$ solution is mixed with the sterile IgG solution to obtain a final concentration of about 2.5 $\mu$g–75 $\mu$g Sn/mg IgG. If necessary pH is adjusted to about 5.0–6.0.

The solution of IgG and stabilized stannous ion along with other components of the formulation is measured into sterile vials, e.g. at a unit dosage of about 2.0 mg IgG/vial and the vials are lyophilized in accordance with the procedures herein described. Sealed lyophilized imaging agent containing moisture of not greater than 2.5% has been stored stably at 5° C. and at room temperature for at least 24 months and retains its capacity to be rapidly and quantitatively labeled with $^{99m}Tc$ ions upon mixing with pertechnetate.

To label a unit dose of antibody fragment, a vial of liquid nitrogen frozen solution is thawed to room temperature by gentle warming, or a vial of lyophilizate is brought to ambient temperature if necessary. A sterile saline solution of a suitable imaging quantity of pertechnetate is added to the vial via tuberculin syringe and the contents are mixed. When labeling the foregoing unit dosage quantity of antibody, the amount of pertechnetate is generally about 1–100 mCi/mg of antibody. With the preferred concentrations of protein and stannous ions noted above, the amount of pertechnetate is preferably about 5–20 mCi/mg, and the time of reaction is about 40–60 minutes for $^{99m}Tc$-glucoheptonate, and about 10–30 minutes for $^{99m}Tc$-tricine. This is effectively an "instant" labeling procedure with respect to the prior art processes which generally required from 30 minutes to several hours incubation, in some cases at elevated temperatures and/or with additional purifications required.

Pertechnetate is generally obtained from a commercially available generator, most commonly in the form of $NaTcO_4$, normally in saline solution. Other forms of pertechnetate may be used, with appropriate modification of the procedure, as would be suggested by the supplier of a new form of generator or as would be apparent to the ordinary skilled artisan. Pertechnetate is generally used at an activity of about 0.2–20 mCi/ml in saline, e.g., 0.9% ("physiological") sterile saline, optionally buffered at a pH of about 3–7, preferably 3.5–5.5, more preferably about 4.5–5.0. Suitable buffers include, e.g., acetate, tartrate, citrate, phosphate and the like. Preferred buffers are acetate tartrate and citrate, most preferable is citrate.

The resultant $^{99m}Tc$-labeled antibody is suitable and in fact particularly efficacious for non-invasive scintigraphic imaging of focal sites of infection and inflammation, tumor imaging, imaging of arthritis and osteomyelitis.

In another embodiment of the invention, the targeting molecule can be "therapeutically conjugated" and used to deliver a therapeutic agent to the site of infection or inflammation. The term "therapeutically conjugated" means that the targeting molecule is conjugated to a therapeutic agent. Therapeutic agents used in this manner are directed either to the underlying cause of the inflammation, for example, the infectious organisms or a tumor, or to components of the inflammatory process itself. Examples of agents used to treat inflammation are the steroidal and non-steroidal anti-inflammatory drugs. Many of the non-steroidal anti-inflammatory drugs inhibit prostaglandin synthesis.

Other therapeutic agents that can be coupled to the chemotactic peptides according to the method of the invention are drugs, radioisotopes, lectins, toxins, and antimicrobial agents. The therapeutic dosage administered is an amount that is therapeutically effective and will be readily determinable by those skilled in the art. The dosage will also be dependent upon the age, weight and health of the recipient, type of concurrent treatment, if any, frequency of treatment and nature and severity of the disease, as well as effect desired, for example anti-bacterial or anti-inflammatory effects.

Examples of radioisotopes that can be bound to the targeting molecule of the instant invention for therapeutic purposes and used according to the methods of the invention, include but are not limited to $^{125}$I, $^{131}$I, $^{90}$Y, $^{67}$Cu, $^{217}$Bi, $^{211}$At, $^{212}$Pb, $^{47}$Sc, $^{186}$Re, $^{188}$Re, $^{105}$Rh, $^{153}$Sm, and $^{109}$Pd. Other therapeutic agents that can be coupled to the targeting molecule used according to the method of the invention are also known, or can be easily ascertained by those skilled in the art. It is understood that the term "imaging agent" herein also contemplates its use as a therapeutically-conjugated targeting molecule in addition to its use in radionuclide imaging.

In yet a further embodiment, the present invention provides a kit comprising a two-vial system, used for preparing an imaging agent. The kit comprises a first vial containing lyophilized imaging agent, and a second vial containing a liquid diluent. The first vial may further comprise other above-disclosed components for instance drying protectant and excipient. The liquid diluent is a pharmaceutically acceptable diluent such as for example sterile water or sterile sodium chloride USP. Alternatively, the diluent may be chosen from any of a range of suitable buffers, which provides the added advantage of providing for a stable pH. Suitable buffers are those selected from the group consisting of phosphate buffers, citrate buffers, borate buffers and acetate buffers. Most preferably, the liquid diluent is USP normal saline, sterile USP.

A kit for use in radiolabeling imaging agent wherein targeting molecule is an antibody (monoclonal or polyclonal) or a chemotactic peptide, with radionuclides, in particular $^{111}$In or $^{99m}$Tc, the latter using pertechnetate, would typically include in a first vial: (1) the aforedescribed lyophilized imaging agent in an amount of approximately 1.0–2.0 mg per vial, (2) a drying protectant (mannitol or tricine, for example), (3) an excipient (polysorbate 80, for example), (4) citrate, and wherein the linker is SHNH, (5) stannous ions and a stabilizer such as tartrate or tricine. The imaging agent components of the kit are provided in a single sterile vial in lyophilized form. The lyophilized imaging agent cake is reconstituted with a pharmaceutically acceptable diluent, which is provided in the second vial. The reconstituted imaging agent is further admixed, just prior to use, with about 20–30 mCi of $^{111}$In or $^{99m}$Tc pertechnetate in sterile aqueous solution, such as sterile water or sodium chloride per mg of targeting molecule. Also provided may be other suitable reagents, for example buffer e.g. citrate.

The kit has the advantage of providing a stable formulation of the imaging agent, which has a long shelf life. The lyophilized imaging agent having a moisture content of 2.5% or less has a shelf life of 24 months when stored both at 5° C. and room temperature (about 25° C.). A fresh stable solution of the imaging agent can be prepared at any desired time by mixing the contents of the second vial with that of the first vial. The resulting solution may then be used at the clinical site immediately and, following admixture with radiolabel may be delivered directly to the subject.

When used in the imaging of a subject, the chelation of the $^{111}$In to the DTPA-IgG was allowed to take place for about 15 minutes prior to injection into the subject. The reconstituted imaging agent is stable for about 72 hours at room temperature. The reconstituted, chelated imaging agent is stable for about 6 hours when stored at 2–8° C.

Methods of freeze drying are well known in the art and are set forth, for example, in *Methods in Enzymology*, Vol. 22, Pages 33–39, Academic Press, New York (1971); and in *Freeze-Drying, E. W. Flosdorf, Rheinhold, New York* (1949). In preparing the kits of the present invention, it is desirable to lyophilize the imaging agent in the same vial in which it will be sold. An aqueous solution of the imaging agent herein disclosed is added to the vial after filtering through a sterilizing filtration system, such as a 0.22 micron filter standardly used in sterilizing proteins or peptides. The contents of each vial may then be lyophilized and afterwards the vials capped and sealed under sterile conditions. A sterile final product is desirable when the product is going to be used for parenteral administration in, for example, scintigraphic imaging or therapeutic use. In general the most useful container for a vial are the glass bottles standardly used for lyophilizing biological materials. Another suitable container is a two-compartment syringe wherein one compartment contains the lyophilized imaging agent cake and the other compartment contains the aqueous diluent. After lyophilization is complete, the vacuum within the vials or ampules may be released by filling the system with an inert gas, stoppered in place using standard equipment and then crimp sealed. Such a method will ensure a sterile final product.

In the lyophilization methods of the present invention, the imaging agent formulations are lyophilized in a controlled cycle. The formulations are placed in a 3 mL Type I glass vial with 13 mm West Company (Phoenixville, Pa.) 4416/50 stoppers partially depressed, and the vials held in the lyophilizer at 4° C.–8° C., preferably about 5° C. for one-half hour, after which time the temperature is ramped-down over 9 hrs to −50° C. at a rate of 0.1° C. to 1.0° C. per minute, preferably about 0.1° C. per minute (−6° C./hour), and held for 4 hours at −50° C. during which time the condenser is turned on (one-half hour into the 4 hour soak). Thirty minutes after the condenser is turned on, vacuum of 40 $\mu$M Hg–80 $\mu$M Hg, preferably about 60 $\mu$M Hg, is pulled. At the end of the 4 hour soak, the temperature is ramped up over about 4.0–5.5 hours, preferably about 5 hours, to a temperature of −17° C. to 27° C., preferably −22° C., at a rate of +0.1 to +0.5° C. per minute, preferably about 0.1° C. per minute (+6° C./hour), under vacuum of about 40 $\mu$M Hg–80 $\mu$M Hg, preferably about 60 $\mu$M Hg, and held for 24 hours. The temperature was then ramped up to about 15° C.–25° C., preferably about 20° C., over 7 hours at a rate of +0.1° C. per minute under vacuum of about 40 $\mu$M Hg–80 $\mu$M Hg, preferably about 60 $\mu$M Hg, and held for 6–17 hours, preferably about 6–15 hours. Nitrogen is backflushed into the chamber, and the vials mechanically sealed with 2 inches of vacuum in vials. The vials are reconstituted with 2.0 ml saline (0.9%) or other pharmaceutically acceptable carrier or diluent.

A variety of containers are suitable for lyophilization. A proper container should be able to withstand the outside pressure when the container is sealed and stored under partial vacuum. The container should be made of a material that allows a reasonable transfer of heat from outside to inside. The size of the container should be such that the solution to be lyophilized occupies not more than 20% of the useful volume or may be overfilled with an excess, in accord with then-prevailing USP recommendations for the volume in a container. For example, a 0.5 ml solution may be filled in a 3 ml vial. The vials may be made of glass e.g. borosilicate, or plastic, e.g. polypropylene.

In preparing the kits of the present invention, the ultimate delivery system prepared from the kit must be sterile, non-antigenic and free of infectious agents, such as bacteria. Therefore, the kit must be prepared under aseptic conditions or the kit and ingredients must be sterilizable. Sterile filtering and autoclaving are suitable methods for this purpose. All packaging materials, such as glass and rubber may be sterilized by steam. Moisture is removed from the stoppers by for example drying stoppers at 90° C.–110° C. for 0.5–4.0 hours in a stopper preparation machine such as the ICOS machine used herein (Example 2). The liquid and imaging agent may be sterile filtered.

The mode of administration of the preparations of the invention may determine the sites and/or cells in the organism to which the compound(s) will be delivered. The compounds of the invention can be administered alone but will generally be administered in admixture with a pharmaceutical carrier or diluent selected with regard to the intended route of administration and standard pharmaceutical practice. The preparations may be injected parenterally, for example, intra-arterially or intravenously. For parenteral administration, they can be used, for example, in the form of a sterile, aqueous solution which may contain other solutes, for example, enough salts or glucose to make the solution isotonic.

For administration to humans as an imaging agent, the prescribing physician will ultimately determine the appropriate dosage for a given human subject, and this can be expected to vary according to the weight, age and response of the individual as well as the nature and severity of the patient's condition. For administration to humans in the diagnosis of infection or inflammation, the patient will be injected with for example 2.0 mg of polyclonal IgG-DTPA labeled with 1.2 mCi/MEq of $^{111}$InCl over a 30 sec period. (Datz, F. L. et al., 1994, J. Nucl. Med., 35(1):74–83). Imaging may be performed at 7.5±1.5 or at 15±3 hr and again at 24±4 hr post injection. For patients for whom the images are negative or equivocal at 24 hr, 48±4 hr imaging may also be performed.

The following examples are presented to illustrate the subject invention. The invention is not to be considered limited by these examples, but only by the appended claims.

EXAMPLE 1

Lyophilization Protocol:DTPA-IgG

The DTPA-IgG imaging agent was lyophilized in accordance with the following protocol. One-half (0.5) mL of a 4 mg/mL imaging agent formulation (DTPA-IgG) containing:

saline (0.9%)

maltose (5%)

polysorbate 80 (0.04%)

citrate buffer (80 mM)

pH 4.5 was lyophilized in a controlled cycle in a Hull Model FS100 lyophilizer. The formulation was placed in a 3 mL Type I glass vial with 13 mm West Company (Phoenixville, Pa.) 4416/50 stoppers partially depressed, and the vials held in the lyophilizer at 5° C. for one-half hour, after which time the temperature was ramped-down over 9 hrs to −50° C. at a rate of −0.1° C. per minute and held for 4 hours at −50° C. during which time the condenser was turned on (one-half hour into the 4 hour soak) and 30 minutes after the condenser was turned on, full vacuum was pulled. At the end of the 4 hour soak, the temperature was ramped up over 5 hours to −22° C. at a rate of +0.1 to +0.5° C. per minute under vacuum and held for 24 hours. The temperature was then ramped up to 20° C. over 7 hours at a rate of +0.1° C. per minute under vacuum and held for 6 hours. The lyophilized vials were then stoppered with West Company 4416/50 stoppers within the lyophilizer under a nitrogen atmosphere.

Upon reconstitution with 2.0 ml saline (0.9%) the final formulation contained imaging agent 1 mg/mL in 20 mM citrate buffer, 1.25% maltose, 0.9% saline and 0.01% polysorbate 80 at pH 4.5.

EXAMPLE 2

Lyophilization Protocol: DTPA-IgG

The following formulation of DTPA-IgG was lyophilized according to the following protocol. A formula containing:

| Component | Lyophilized (mg/vial) | After Reconstitution (mg/ml) |
|---|---|---|
| DTPA-Immune Globin (Human) | 2.0 | 1.0 |
| Sodium Citrate Dihydrate, USP | 6.3 | 3.2 |
| Citric Acid Anhydrous, USP | 3.5 | 1.8 |
| Maltose Monohydrate | 26.3 | 13.2 |
| Polysorbate 80 USP/NF | 0.2 | 0.1 |
| 0.9% Sodium Chloride, USP | — | 2.0 ml | was lyophilized in accordance with the processes of Example 1. The final imaging agent product was filled in 3 mL capacity USP Type I borosilicate clear glass vials with 13 mm finish (West Company). The vials were overfilled with an excess, in accord with current USP recommendations for volume in a container. To reduce moisture content of 13 mm West 4416-50 grey, split butyl rubber stoppers (West Company) stoppers treated with silicon to facilitate insertion into vials, were prepared using an ICOS LST-80 stopper processing machine (ICOS, Pordenone, Italy) and dried for ½ hour-4 hours, preferably about 3 hours, at 110° C. Such drying time reduced the stopper moisture to less than 0.25%. After such time period, stoppers were placed in a plastic bag and stored in an aseptic area for 24 hours followed by exposure in the aseptic area for 6 hours. The stoppers were sealed with aluminum controlled-score crimp seals with dust cap (West Company)

EXAMPLE 3

Rehydration of Lyophilized DTPA-IgG

The DTPA-IgG complex supplied in a 3 ml vial containing 2.0 mg of lyophilized DTPA-IgG of Example 2 was rehydrated as follows. Using aseptic technique, and after standing at room temperature (about 25° C.) for 10 minutes, 2 ml of sterile normal (0.9%) saline was injected into the vial. Vial contents were mixed by gentle inversion for about 15 minutes.

EXAMPLE 4

Chelation of Radiolabel To DTPA-IgG

Following the reconstitution of the lyophilized DTPA-IgG of Example 3 above, 2.5 mCi of $^{111}$In-chloride was admixed therewith by aseptic injection into the vial. The contents were gently mixed and allowed to stand at RT for 15 minutes. Radiochemical purity testing was performed using thin-layer chromatography as discussed in Example 7 hereinbelow. Over 90% labeling efficiency was measured within one hour of preparation. Number of DTPA's per IgG were calculated in accordance with the methods of Example 7 herein.

When used in the imaging of a subject, the chelation of the $^{111}$In to the DTPA-IgG was allowed to take place for about 15 minutes prior to injection into the subject. The reconstituted imaging agent is stable for about 72 hours at room temperature. The reconstituted, chelated imaging agent is stable for about 6 hours when stored at 2–8° C.

EXAMPLE 5

DTPA-IgG Manufacturing Process

All glassware and stainless steel pots employed in the DTPA-IgG Manufacturing process are depyrogenated. All necessary equipment is autoclaved. The 4 liter reaction vessel, Talboys stirring motor and Amicon CH2 apparatus with reservoir were set up in diafiltration mode. Two liters of 0.15 N Sodium Hydroxide buffer were prepared and used to sanitize the Amicon CH2 apparatus. Fifteen liters of vehicle buffer (citric acid/sodium citrate, maltose and polysorbate 80) were prepared for use the next day. The following was the DTPA-IgG formulation:

| Water for Injection (20 ± 5° C.), USP | 15 L |
|---|---|
| Sodium Citrate (dihydrate), USP | 12.69 g/L |
| Citric Acid (anhydrous), USP | 7.08 g/L |
| Maltose | 52.66 g/L |
| Polysorbate 80 (TWEEN 80) | 0.40 g/L |
| IgG | 500 ± 10 mL at 50 mg/mL |
| DTPA-DA | 167 ± 3 mg |

The pH of the vehicle buffer was determined and if in range of 4.3 to 4.7, the buffer was brought to final weight using WFI. The buffer was aseptically filtered into autoclaved carboys, sealed and stored at 2–8° C. overnight (the buffer may be stored for up to four weeks at 2–8° C.).

Two liters of Sodium Bicarbonate reaction solution were prepared (8.4 g/L). After the solids were completely dissolved in WFI, 500±10 milliliters of Intravenous Human Immune Globulin (IgG: 50 mg/ml) (Cutter Biologicals, Berkeley, Calif.) were poured into the solution. Caution was taken to prevent the protein from foaming while mixing, by regulating the speed of mixing. When the solution was thoroughly mixed, a sample was removed to determine the protein concentration ($A_{280}$) in accordance with the methods in Example 7 herein. The protein concentration must be within the range of 9–11 mg/ml in order to proceed.

Another sample was removed for pH determination, performed in accordance with the methods of Example 7 herein. The pH must be in the range of 7.7–8.2 in order to proceed with the conjugation of Diethylenetriamine-pentaacetic dianhydride (DTPA-DA) to the IgG.

The conjugated DTPA-IgG was carried out in accordance with the methods of Hnatowich, referenced hereinabove. The DTPA-DA was weighed out (167±3 mg) and slowly added to the solution in the reaction vessel. The mixture was stirred continuously at a rate to minimize foaming for 35±5 minutes. After the conjugation process, a sample was removed for an ITLC assay to determine the DTPA/IgG substitution ratio, in accordance with the procedures of Example 7 herein.

During the conjugation process, the Amicon CH2 apparatus was flushed with suitable volumes of cooled WFI (25±10° C.). The pH of the permeate and return lines was then determined. The pH must be no greater than 8.0 in order to proceed with the diafiltration of conjugated DTPA-IgG solution.

When the Amicon system pH was ≦8.0, the batch was concentrated using the Amicon CH2 apparatus until 1500–1600 ml of permeate was collected. In addition to concentration, this process also removes free DTPA-DA molecules that did not conjugate with the IgG.

After concentration, the material was diafiltered into the vehicle buffer prepared the previous day. A volume of 6,000 ml was used in the buffer exchange of the 1,000 ml batch size. When 6,000–6,200 ml of permeate was collected, the diafiltration was complete and the batch was pumped into a tared, clean stainless steel pot.

The cartridge and Amicon CH2 unit were flushed with three 1,000 ml rinses of the vehicle buffer. The washes were pumped into the tared pot containing the batch. The batch weight was determined and converted to the volume by multiplying by the batch density of 1.029 gm/ml.

The batch was mixed for a sufficient amount of time at a rate to minimize foaming, typically about 10 minutes at a rate to minimize foaming. A sample was removed to determine protein concentration ($A_{280}$) of the diafiltrated bulk, in accordance with the methods of Example 7 herein. The batch volume was multiplied by the protein concentration ($A_{280}$) to calculate the yield of DTPA-IgG in milligrams.

The calculated yield in milligrams was divided by 4 mg/ml to obtain the final batch volume. The final volume was converted to final weight using the density as done previously hereinabove.

The final gross weight of the batch was determined. A sufficient amount of vehicle buffer was added to the batch until the calculated weight was reached. The batch was stirred again at a rate to minimize foaming, as hereinabove.

Three samples were removed from the bulk for pH determination, protein concentration and bulk sterility testing, all in accordance with the methods of Example 7 herein. The pH must be in the range of 4.3 to 4.7 and the concentration must be between 3.75 to 4.15 mg/ml to proceed to the sterile filtration step.

The bulk DTPA-IgG was transferred to a stainless steel pressure vessel with a 22.0μ sterile filtered nitrogen source attached to the inlet. The vessel was sealed and the nitrogen turned on to begin filtration. The bulk was passed through a Millipak-200 cartridge 0.45μ low protein-binding pre-filter unit (or equivalent) and sterile filtered through a Millipak-200 0.22μ low protein-binding cartridge (or equivalent).

The filtered material was collected in an autoclaved polypropylene carboy. Three samples were collected from the filter nozzle near the end of filtration for LAL, ITLC and sterility testing, all in accordance with the methods of Example 7 herein. An additional sample was removed for formulated bulk release testing in accordance with the methods of Example 7 herein. The carboy was sealed and stored at 2–8° C. until preparation for filling and lyophilization. DTPA-IgG finished manufactured product specifications are shown in Table I herein.

TABLE I

DTPA-IGG FINISHED PRODUCT SPECIFICATIONS
(After reconstitution with 2 mL of 0.9% Normal Saline, Sterile USP)

| Test | Specifications |
|---|---|
| Appearance | Colorless and clear to slightly opaque |
| pH | 4.20–4.80 |
| Protein Concentration | 1.90–2.70 mg/vial |
| HPLC (Gel Permeation) | Area % of IgG $\geq$ 80% |
| HPLC (Citric Acid Concentration) | 38–60 micromoles/vial |
| General Safety, USP | Passes |
| Bacterial Endotoxin (LAL) | $\leq$2.5 EU/mL |
| Sterility, USP | Passes |
| ITLC | indium-111 uptake $\geq$ 90% at 1 hour |
| Biodistribution: | |
| Infected muscle/layer | >0.72 |
| Infected muscle (% injected dose/gram) | >0.84 |
| Infected muscle/normal muscle | >3.20 |
| Moisture (prior to reconstitution) | $\leq$5% |

EXAMPLE 6

Filling and Lyophilization of DTPA-IgG Bulk Product

The bulk formulation of Example 5 hereinabove was transferred to an autoclaved stainless steel pressure vessel with a 0.22$\mu$ sterile filtered nitrogen source attached to the inlet. The outlet was closed and the vessel sealed.

The vessel outlet was connected to a sterile glass carboy in a sterile filtration area using Tygon tubing fitted with a Millipak-200 0.22$\mu$ pore size filter unit in-line. The outlet of the vessel was opened and the nitrogen turned on slowly to bleed the lines and filter housing of air. The bulk was filtered into the receiving vessel with about 20 psig of pressure. The filtered DTPA-IgG was aseptically filled into 3 ml vials using a Chase-Logeman filler apparatus at a nominal fill volume of 0.5 ml.

After filling, the vials were partially stoppered and placed in the Hull Model FS100 Lyophilizer. Temperature thermocouples were inserted into vials to monitor temperature distribution during the lyophilization cycle. The temperature was maintained for approximately 0.5 hours at the loading temperature of 4° C. before freezing was begun. The product was lyophilized in accordance with Example 2 herein. When the lyophilization cycle was complete, the vials were back-flushed with dry, sterile nitrogen and fully stoppered in the lyophilizer. The vials were removed and sealed with a controlled score color-coded crimp using a West Model W500 Capper Machine.

The final product was packaged and stored at 2–8° C. until distribution to the appropriate clinical sites where reconstitution and labeling took place.

EXAMPLE 7

Description of Testing Methods for Raw Materials, Bulk, and Reconstituted (Final) DTPA-IgG Product Appearance Samples from each lot of purified bulk and final product were visually examined for clarity, color and foreign matter under fluorescent lighting against both black and white backgrounds. Purified and final samples may contain translucent proteinaceous particles, and must be colorless and clear to slightly opaque.

pH

Each lot of purified bulk and final product was tested for pH. The test was performed at room temperature (15° to 300° C.) using a pH meter. The pH meter was calibrated using pH 10.00, pH 7.00 and pH 4.00 standard solutions. A pH 6.00 buffer was read directly from the meter and must be between 5.95 and 6.05 pH units. The electrode of the pH meter was washed with distilled water between each use and gently wiped dry. The sample to be tested was brought to room temperature and the cleaned electrode was dipped into it. The pH was read directly from the meter and recorded. If the pH was greater than 7.00, a pH 8.00 buffer was read directly from the meter and must be between 7.95 and 8.05 pH units. The pH of the bulk product and final product should be 4.30 to 4.70.

During formulation, the pH of the vehicle buffer must be 4.30–4.70. The pH of the sodium bicarbonate reaction mixture must be 7.7–8.2.

Protein Concentration ($A_{280}$)

Each lot of reaction mixture, purified bulk and final product was tested for protein-concentration by spectrophotometer UV absorbance at 280 nm. The reaction mixture is read at $A_{280}$ against the citrate buffer. The purified bulk product was appropriately diluted with vehicle buffer and read in a UV spectro-photometer at a wavelength of 280 nm against Water for Injection. The final product was read without alteration. The protein concentration (mg/mL) was determined by dividing the absorbance at a wavelength of 280 nm by the extinction coefficient (1.40) of human IgG. The protein concentration of the reaction mixture should be 9–11 mg/ml, and purified bulk product should be between 3.75 and 4.15 mg/mL (after dilution). The protein concentration of final product should be 1.90–2.70 mg/vial.

HPLC (Gel Permeation)

Quantitation of the IgG monomer was accomplished by UV detection at 280 nm and percent purity was determined by area percent analysis of the peaks present in the chromatogram. The method permits the identification of aggregated IgG, fragmented IgG or other impurities present in the purified product.

Each lot of purified bulk product or final product, and reference standard preparation, were appropriately diluted in the mobile phase solution before injection onto a molecular sieve column. The proteins were eluted isocratically and the area percent of the IgG monomer of any higher or lower molecular weight component was calculated by peak integration.

The area percent of the IgG monomer must be greater than or equal to 80% for the purified product to meet specifications.

HPLC (Citric Acid)

This procedure separates citric acid isocratically utilizing an organic acid analysis column. Detection of citric acid was accomplished via a UV detector, and quantitation via peak area response. Bulk samples were diluted one to four with water for injection prior to analysis. The citric acid concentration in purified bulk should be 70–90 mM, and in final product, 38–60 micromoles/vial.

In order to extend the life of the column, the protein was removed from the sample by utilizing a 30,000 M.W. cutoff filter. SCX filters were utilized in order to eliminate NaCl.

Bacterial Endotoxin (LAL)

Limulus Amebocyte Lysate (LAL) which has been obtained from aqueous extracts of the circulating amebocytes of the horseshoe crab *Limulus polyphemus*, and which has been prepared and characterized for use as an LAL reagent for gel-clot formation with a test sensitivity of 0.03 EU/mL is employed.

Serial dilutions of the endotoxin standard and product were added to the reaction tubes, mixed with the lysate and the tubes were incubated for 60±2 minutes in a non-circulating waterbath at a temperature of 37±1° C.

The determination of the reaction end-point was made with dilutions from the product in direct comparison with parallel dilutions of a reference standard endotoxin (RSE), and quantities of endotoxin were expressed in defined Endotoxin Units. The specimen was judged to comply with the requirements if the result does not exceed (a) the concentration limited specified (≦2.5 EU/mL), and (b) the specified confidence limits for the assay.

Sterility, (Membrane Filtration)

1. Bulk Product.

The procedure was applicable for determining whether an article purporting to be sterile complies with the requirements set forth with respect to the test for sterility. Liquids from test containers were aseptically removed using the steritest system. Filters in canisters were rinsed with three 100 mL portions of Fluid A. One canister was filled with 100 mLs of Fluid Thioglycollate Medium and the other with Soybean-Casein Digest Medium. The FTM canister was incubated at 30–35° C. and the SCD canister at 20–25° C. for 7 days. At the end of incubation period it was determined by visual examination presence or absence of microbial growth, which can be verified by subculturing of presumptive positives. The product must show absence of microbial growth after a 7 day incubation period.

2. Final Product.

The procedure determines if the product complies with the sterility requirements established in USP XXII. The minimum number of vials required for sterility testing was 40 based on the 0.5 mL fill volume. The product must show absence of microbial growth after a 7 day incubation period. The lyophilized product was reconstituted with 2.0 ml of 0.9% Saline.

Qualification of DTPA-Anhydride by Determining Number of DTPA's per IgG

This protocol describes the necessary materials and procedure for the qualification of a new lot of DTPA anhydride, prior to manufacturing, using a functional determination. This test is used to ensure the DTPA has not hydrolyzed prior to use. First, DTPA is conjugated to IgG. Next, a sample is taken for the determination of the number of DTPA's per IgG molecule. The test methods uses $^{111}InCl_3$ and Instant Thin Layer Chromatography.

Prepare 200 g of 0.1 M Sodium Bicarbonate by weighing 1.68 g of Sodium Bicarbonate, add the Sodium Bicarbonate to 200 g of Millipore water and mix until dissolved. Prepare 10 mg/mL IgG in 0.1 M Sodium Bicarbonate as follows. To the 200 g of Sodium Bicarbonate add 50 mL of IgG (Gamimune), mix for approximately 5 min. Remove a 3 mL sample for pH determination. The pH should be between 7.7 to 8.2. Remove a 2 mL sample for determination of protein concentration.

Protein concentration determination is performed as follows. Using a 1 mL volumetric pipette, dispense 1 mL of the IgG sample into a 25 mL volumetric flask. Bring up to volume with Millipore water. Mix by inversion until evenly dispersed. Blank the spectrophotometer with Millipore water, read the sample and perform the calculation for protein determination as follows:

O.D. × dilution factor/absorbance coefficient
=O.D. × 25/1.4
=O.D. × 17.86
=__mg/mL.

The protein concentration should be between 9.0 mg/mL and 110 mg/mL.

Conjugate the IgG to DTPA Anhydride as follows. Weigh 0.0167 g of DTPA Anhydride. Mix the IgG solution in a 400 mL beaker so that a vortex extends halfway down the length of the container. Add the DTPA Anhydride and mix for the 35 mm±5 min. After the allotted time remove a 10 mL sample and analyze for the number of DTPA's per IgG molecule (ITLC assay). Follow instructions outlined in "Number of DTPA's per IgG."

Instant Thin-Layer Chromatography (ITLC)—Chelation Efficiency

Instant thin-layer chromatography (ITLC) was used to determine the $^{111}$Indium chelation ability of each lot of final product. This test is employed in the radiopharmacy prior to administering the chelate to the subject. ITLC is a paper chromatographic method using silica gel impregnated paper strips. A sample of DTPA-IgG conjugate was radiolabeled with $^{111}$Indium and spotted onto the ITLC strip. During development in an appropriate buffer system (e.g., citrate, normal saline or phosphate buffered saline) the radiolabeled DTPA-IgG remains at the origin, whereas other unconjugated labeled products move with the solvent front. The percentage of radioactivity at the origin indicates the amount of $^{111}$Indium that has been chelated by the DTPA-IgG conjugate ($^{111}$Indium uptake). The $^{111}$Indium uptake of imaging agent final product should be ≧90% at 1 hour.

This assay is sensitive to changes in DTPA-IgG. Exposure of DTPA raw material to moisture affects the conjugation of DTPA to IgG. Exposure of DTPA-IgG to intense light results in a decrease in the DTPAs per IgG measured. The assay can detect those changes.

More particularly, the following procedure is used to determine chelation efficiency, which when multiplied by molar ratio, gives a result for DTPA/IgG:

1. Cut ITLC-SG strips into lengths approximately 9×1 cm. Handle strips with forceps or gloved hands. Place 2–3 ml of 80 mM citrate buffer in pH 5.9 in the bottom of a 50 ml beaker or other suitable container.
2. Using a pencil or non-water soluble marker, mark the origin approximately 3 cm from the bottom, mark the cut line 5.5 cm from the bottom. With a water soluble felt tip pen, mark the solvent front line at 8 cm.

Reconstitute DTPA-IgG by injecting 2 ml of sterile 0.9% saline into the vial. Repeatedly invert the vial gently until the cake has dissolved (about 15 seconds).

Calculate the volume of $^{111}$In-Cl$_3$ as follows: withdraw the aliquot desired from the vial and place into smaller aliquot vial. Adjust the calculated volume of $^{111}$In-Cl$_3$ necessary (generally about 300+/−30 µCi), according to the formula:

$$\frac{\text{Amount desired } (\mu Ci)}{\text{Specific Activity } (\mu Ci/\mu L)} = \text{Desired Volume}$$

To determine chelation of $^{111}InCl_3$ to the DTPA-IgG, withdraw the above-calculated volume of $^{111}InCl_3$ into a syringe. Read the vial in a dose calibrator set for $^{111}$In to obtain background reading. Inject the volume of $^{111}InCl_3$ into reconstituted sample vial and record the time at which the $^{111}$InCl$_3$ was added. Invert the vial 5 times. Measure the vial to determine counts per vial. Wait about 10–15 minutes.
3. Place a small (1–2 μl) drop of $^{111}$In-DTPA-IgG at the origin on the rough appearing side of the strip. It is not necessary for the spot to dry before developing the strip. Place the strip in the beaker containing the buffer. The origin must be above the liquid level.
4. Allow buffer to travel up the strip until the water soluble mark, at 8 cm, spreads.
5. Determine the distribution of radioactivity on the strip by one of the following methods:
   a. Cut strip at the cut line, at the 5.5 cm, mark and count each half in a gamma counter. $^{111}$In-DTPA-IgG remains at the origin, while the $^{111}$InCl$_3$ moves with the solvent front.
   b. Use a suitable radiochromatogram analyzer.
6. The calculation of chelation efficiency is performed as follows:

$$\frac{\text{CPM at origin}}{\text{CPM at origin} + \text{CPM at solvent front}} \times 100 =$$

Percent Chelation Efficiency

Number of DTPA's per IgG-Bulk Product

Instant thin-layer chromatography (ITLC) was used to determine the average number of DTPA's per IgG. ITLC is a paper chromatographic method using silica gel impregnated paper strips. A sample of DTPA-IgG conjugate was radiolabeled with $^{111}$Indium and spotted onto the ITLC strip. During development in an appropriate buffer system (e.g., citrate, normal saline or phosphate buffered saline), the radiolabeled DTPA-IgG remains at the origin, whereas other unconjugated labeled products move with the solvent front. The percentage of radioactivity at the solvent front indicates the amount of $^{111}$Indium that has been chelated by the DTPA-IgG conjugate. The average number of DTPA's per IgG was calculated by multiplying the percentage of $^{111}$Indium that has been chelated by the DTPA-IgG conjugated by the molar ratio of DTPA-DA used in the reaction. The number of DTPA's/IgG for DTPA/IgG imaging agent bulk product should be 1 to 3.

This method describes the necessary materials and procedures for the determination of the number of DTPA's per IgG molecule for DTPA-IgG. The method uses $^{111}$InCl$_3$ and Instant Thin Layer Chromatography (ITLC).

Obtain a 2.0 to 2.5 mL sample of the DTPA-IgG to be analyzed and carefully pipet 0.5 mL into each of three 5 mL volumetric flasks using a 0.5 mL volumetric pipet. Bring up to the 5 mL mark with 80 mM citrate buffer (pH 5.0). Repeat this sequence two more times to produce a 0.5 mL volumetric pipet. Bring up to the 5 mL mark with 80 mM citrate buffer (pH 5.0). Repeat this sequence two more times to produce a total of three diluted samples for the determination of the number of DTPAs per IgG molecule.

To chelate the $^{111}$InCl$_3$ to DTPA-IgG, pipette 300 μL of the samples prepared into 1.8 mL Wheaton vials. Repeat this process for the other sample tubes. Into each of the diluted samples, add 300±30 micro Curies of $^{111}$InCl$_3$. Mix by inverting three to five times. Read in dose calibrator and record measurement. 300 uCi was selected to maintain the same 111In to protein concentration as prescribed for the clinical dosage of 2 mCi/mg. The amount of $^{111}$InCl$_3$ added should be recorded. Wait 30 to 45 minutes before performing the ITLC procedure.

The Instant Thin Layer Chromatography Procedure is performed as follows. Strips of ITLC-SG media (Gelman ITLC-SG media) are marked at 3, 5.5 and 8 cm from the bottom. At the 8cm mark a spot of water soluble ink is placed in the center of the strip. Using a fresh 1 mL insulin syringe for each sample, draw up approximately 0.1 mL of the sample into the needle and expel it back into the vial. Carefully spot one drop of this sample of $^{111}$InCl$_3$-chelated DTPA-IgG from the syringe needle tip onto the 3 cm mark. This process should be done for each of the three dilutions prepared.

Place 2 mL of the 100 mM citrate buffer (pH 5.0) into a Corning 3×15 mL tube which will be used as a developing chamber. Insert the spotted ITLC strip into the chamber being careful to not allow the sample spot presence of the solvent front, use forceps to remove the strip from the chamber. Do not allow the solvent front to move to the end of the strip.

Cut the strip in half at the 5.5 cm mark and place each half into a labeled tube designated for gamma counting purposes. Determine the number of cpm's for the origin and the solvent front-halves using a gamma counter set for $^{111}$In. Count for 15 seconds.

The number of DTPAs per IgG molecule is calculated using the following formula:

$$\frac{\text{counts at origin}}{\text{total counts}} \times 3.0 = DTPAs \text{ per IgG molecule}$$

Total counts=counts at origin+counts at solvent front The value of 3.0 above represents the molar ratio of DiethyleneTriaminePentaAcetic-DiAnhydride to the IgG used in the reaction to produce the DTPA-IgG. The acceptable range of DTPAs per IgG is 1 to 3.

Moisture of Bulk Product (prior to reconstitution)

Each lot of final lyophilized product was tested for percentage of residual moisture content. The test was performed using a Karl Fischer Coulometric Titrator (Mettler Model DL18) with attached drying oven. The pre-weighed product sample was introduced into the drying oven which was preheated to 110–130° C. Hot, dry nitrogen gas carries evaporated water from the product to the Titrator. The instrument uses evaporated water from the product to the Titrator. The instrument uses the sample weight to determine the percentage of water in the sample. There should be less than 5% moisture in DTPA-IgG final product.

Infecting of Test Rats With Escherichia coli as well as Subsequent Injection and Evaluation of the Biodistribution of the Labelled Test Material This describes the materials and appropriate procedures for the infecting of test rats with *E. coli* and subsequent injecting of imaging agent and evaluation of infection/inflammation.

A. Infecting animals with *E. coli*:
1. Infecting animals with *E. coli*: dilution study to characterize lots of *E. coli* culture.
   a. Five concentrations (approx. mid-range 8×10$^8$ colonies) will be used to infect male Sprague-Dawley rants. Ten rats per concentration are selected based on an acceptable weight range (160–200 g). Rats are uniquely ear tagged for identification. Seven to ten rats are injected at each of the concentration levels of *E. coli* culture. Using appropriately sized syringes and needles, a volume of 200 μL is injected intramuscularly in the right hind-thigh of each animal. Each rat is then weighted on the appropriate balance which has an automatic entry into a Lotus spread sheet.
   b. The animals are housed in disposable rat cages. Feed and water are available on demand.

c. Death rates are monitored, and the optimal dose chosen ideally should not exceed 20% of the animals in a group.

d. Following imaging (Step 111.B.3 below), the optimum concentration providing maximum imaging characteristics of infection/inflammation while minimizing animal deaths can be identified. The optimal optical density is chosen for a specific batch of *E. coli* based on the results of the above dilution study.

2. Infecting animals with *E. coli*: for release testing of imaging agents.

a. Based on the biodistribution ratios obtained for each of the five dilutions studied (above) an optimum dilution concentration can be selected for a particular batch of *E. coli*.

b. For a particular batch of *E. coli*, remove a vial from the freezer, thaw at room temperature, and if necessary, homogenize by swirling. Avoid shaking. Remove an appropriate volume of culture and dilute with saline to the appropriate concentration, previously determined for this batch of *E. coli* (see above).

c. To achieve a minimal final number of five rats per group, seven male Sprague-Dawley rats per group are selected based on an acceptable weight range (160–200 g). Rats are uniquely ear tagged for identification. Each rat is injected intramuscularly in the right hind-thigh using an appropriate sized needle and syringe at a volume of 200 $\mu$L of the prepared dilution of *E. coli* culture (above). Each rat is weighed on the appropriate balance which has an automatic entry into a Lotus spread sheet.

d. Following inoculation, the animals are returned to their cages.

B. Injection/Biodistribution

1. Approximately 24 hours following inoculation with *E. coli* each rat is placed under the heat lamp for approximately 5 minutes for vessel dilation. They are then anesthetized in a chamber with ether.

2. Within 6 hours of the radiolabeling of the test sample with $^{111}$Indium, the anesthetized rats are injected in the tail vein with a volume to achieve approximately 100 $\mu$Ci $^{111}$Indium, using individually marked and dose-calculated syringes. Body weights on the appropriate balance are recorded with automatic entry to the Lotus spread sheet. Any difference from the initial weights (weights following *E. coli* inoculation) is noted in the spread sheet. Animals are returned to their cages to regain consciousness. Food and water are available on demand.

a. At the time that the individual syringes are prepared, a 1 $\mu$Ci standard is prepared, which is used for subsequent calculation of the injected dose. Approximately 100 $\mu$Ci/100 $\mu$L of the imaging agent is added to 9.9 mL of buffer or saline. A volume of this solution to deliver 1 $\mu$Ci is calculated according to the following formula, where the $\mu$Ci values are measured in the dose calibrator:

$$\frac{10{,}000\ \mu L \times 1 \mu Ci}{\text{Aliquot (approximately 100 } \mu Ci)} = \mu L$$

This calculated volume, ideally 90 to 100 $\mu$L, is pipetted into each of five of the same type of test tubes used for counting animal samples in the gamma counter. Approximately 2 mL more of the buffer (or saline used above) is added to each tube in order to have the volume in the tube approximately match the volume for animal samples. The tubes are capped and stored at room temperature for counting along with the animal samples (see below).

3. If Imaging is to be performed:

At approximately 24 hours following the injection of the test sample and imaging agent, each rat is injected intraperitoneally with Nembutal at 32 to 47 mg/kg of body weight. (Note: A 0.1 mL volume of a 65 mg/mL solution of Nembutal to rats of 140 to 200 g of body weight will result in this dosage range). The rat is then marked, using a standard laboratory pen, to distinguish it from the rats not yet injected with Nembutal, and returned to the cage until adequately anesthetized, approximately 5 minutes. This process is repeated for all rats being evaluated.

If imaging is not to be performed, skip to Section b.6 below.

4. A maximum of three anesthetized rats are placed on the detector head of a gamma camera (medium energy collimator 300 Kev) (Technicare Gemini 700). The detector head is placed in an upright position with the animal in a ventral body position presentation to the collimator.

5. Counts are acquired at the level of approximately 100,000/animal. The appropriate camera settings are:

Magnification mode: 2.0
High voltage: approx. 702
Isotope preselect: Manual
Window setting: Lower—off
  Main—173 Kev
  Upper—274 Kev Any tails that appear to have had a substantial portion of the imaging agent administered extravascularly will be placed in a test tube at necropsy for evaluation.

6. Ideally, a 0.5 to 1.0 mL heparinized blood sample is obtained by cardiac puncture from each rat following $CO_2$ overdose. Blood may also be obtained at the time of necropsy when necessary.

7. Animals are euthanized by $CO_2$ overdose, cervical dislocation, or other approved method and necropsied. Prior to necropsy, the infected muscle is palpated and scored by two independent observers and ranked according to the following scale.

0=normal or not swollen
1=mildly swollen
2=moderately swollen
3=significantly/or serious swelling All rat tails are to be screened in the dose calibration for the deposition of extravascular $^{111}$Indium. Cut the tail off at the hair line, and place in a counting tube with the wide end down. Assay all tubes containing tails in the dose calibrator. Record the time and date on the dose calibrator printout. Record the animal's number next to each reading on the printout. For any tails containing more than 4 $\mu$Ci on this reading, subtract this amount from the amount injected on the spreadsheet.

8. For each rat, there will be a unique sample number for blood, kidney, infected muscle, normal muscle, and liver samples which corresponds to the unique animal identification number plus the corresponding letter(s). Weighboats and test tubes are numbered with this same number and an appropriate letter designation of each type of issue, Kidney, liver, and infected and normal thigh muscle samples are obtained by blunt dissection. Each tissue sample is placed in an individual weighboat. Each boat with tissue samples and the syringe with blood sample is weighed on the appropriate balance. The samples, including blood, are placed in labeled test tubes and the weighboats and syringes are reweighed with their residue following tissue removal. All gross and tare weights are automatically recorded onto the Lotus spread sheet from which net sample weights are then calculated within the spread sheet.

9. All sample tubes and standards are counted in a gamma counter. Counter values for each sample are entered onto the Lotus spread sheet.

10. The percent injected dose (% ID) per gram of tissue biodistribution ratio is calculated for each sample and recorded in the Lotus spread sheet using the following formula:

[organ counts/µCi injected×counts/µCi)/net weight]×100

Biodistribution Limits

A. Necropsy biodistribution limits are based on studies performed to validate the procedure and are based upon a mean of tissue samples from a minimum five animals per group.

B. Limits by tissue (% infected dose/gram) are:

| Infected muscle/liver | >0.72 |
| Infected muscle | >0.84 |
| Infected muscle/normal muscle | >3.20 |

Based on the biodistribution ratios a batch of imaging agent may be released (pass/fail). A sample must pass all three limit criteria to pass the analysis.

C. Limitation on the Use of Infected Muscle Data

If an individual animal fails BOTH of the following, all data from that animal will be deleted from the pass/fail evaluation of the sample tested.

1. An individual animal's percent of the injected dose per gram (% ID/g) is less than 1 S.D. from the group mean. The mean of the infected muscle of % ID/g is determined for all animals that received identical infected doses (i.e., same day of treatment, same E. coli dilution). If an individual's % ID/g for the infected muscle is <1 standard deviation below the mean, that animal's data will be deleted if the animal ALSO fails the following:

2. Sum of palpation is equal to or less than 2.

a. If the sum of the palpation scores from the two independent observers (B.7. above) is ≦2, that animal's data will be deleted if the animal ALSO fails the criteria in C.1. above.

b. If two people are available for scoring and only one palpatation score is obtained for any animal, if that score is either 0 or 1 that animal's data will be deleted if the animal ALSO fails the criteria in section C. 1. above. If only one person is available for scoring, the entire study is discarded.

Stability Testing of Lyophilized DTPA-IgG

1. Chelation Efficiency

A lyophilized vial of DTPA-IgG was reconstituted with 2 mL of 0.9% saline-USP. This was done at 0, 1, 3, 6 and 9 months post-manufacture using a stored lyophilized vial each time. The chelation efficiency assay was performed on the sample at each time point. The chelation efficiency was determined, following storage at 2° C., for time points of 0, 1, 3, 6 and 9 months postmanufacturing. As noted in Table II, the chelation efficiency did not change for the time range tested. All time points had mean chelation efficiencies (N 2) of at least 95% for 9 months (Table II). It was determined that DTPA-IgG final product is stable for purposes of chelation efficiency analysis for up to 9 months when stored at 2–8° C.

TABLE II

SOLUTION STABILITY

| Time | n | Mean Chelation Efficiency (%) |
| --- | --- | --- |
| 0 | 2 | 98.90 |
| 1 | 2 | 99.15 |
| 3 | 2 | 95.00 |
| 6 | 2 | 99.00 |
| 9 | 2 | 97.95 |

2. Ruggedness (a) Heat

The contents of several vials of DTPA-IgG were combined to prepare a composite sample. The contents were then distributed into new vials. One aliquot, which served as the control, was stored at 4° C. throughout the course of the study. The remaining vials were incubated at 65° C. at 20% relative humidity (RH) for time periods of 8, 16, 24, 39, and 72 hours. Following incubation the samples were cooled to 4° C. and stored at 2–8° C. prior to analysis. Table III shows the chelation efficiencies for the heat treated and control samples.

TABLE III

EXPOSURE TO HEAT

| Heat Exposure (h) | n | Chelation Efficiency (%) |
| --- | --- | --- |
| 0 | 2 | 96.3 |
| 8 | 2 | 96.6 |
| 16 | 2 | 97.0 |
| 24 | 4 | 96.4 |
| 39 | 4 | 96.1 |
| 72 | 4 | 93.8 |

Table IV shows the biodistribution for heat treated and control samples. "IM" is infected muscle, or the measure of uptake of the compound in the target organ. "IM/NM" is infected muscle to normal muscle ratio, which provides an indication of the imaging efficacy of the compound. This ratio also provides target to background information. "IM/L" is the infected muscle to liver ratio, an indicator of stability.

TABLE IV

Heat/Moisture Degradation

| CONDITION | n | IM | IM/NM | IM/LIVER |
| --- | --- | --- | --- | --- |
| Control | 11 | 0.85 | 4.34 | 0.73 |
| 8 h | 7 | 0.98 | 4.18 | 0.78 |
| 16 h | 5 | 0.95 | 5.20 | 0.72 |
| 24 h | 12 | 0.81 | 3.09 | 0.52 |
| 39 h | 12 | 0.69 | 4.30 | 0.39 |
| 72 h | 11 | 0.43 | 4.82 | 0.20 |

Stability is affected by temperature, moisture, light and product aging.

(b) Light

The contents of several vials of DTPA-IgG were combined to prepare a composite sample. The contents were then distributed into new vials. One aliquot, which served as the control, was stored at 4° C. throughout the course of the study and was not exposed to light. The remaining vials were incubated in the Suntest CPS light box at maximum intensity (725 Watts/m²) for periods of 4, 8, and 16 hours. Subsequent to removal from the light box the samples were cooled to 4° C., and stored at 2–8° C. prior to analysis. Table V shows the chelation efficiencies for the light exposed and control samples.

TABLE V

EXPOSURE TO LIGHT

| Light Exposure (h) | n | Mean Chelation Efficiency (%) |
|---|---|---|
| 0 | 2 | 98.8 |
| 4 | 2 | 98.3 |
| 8 | 4 | 98.3 |

Table VI shows the biodistribution for light exposed and control samples. IM, IM/NM, and IM/L are as defined above.

TABLE VI

| | | Light Degradation | |
|---|---|---|---|
| Exposure Time (h) | n | IM/Liver % | Protein Recovery by GPC |
| 0 | 24 | 0.734 | 100.00 |
| 4 | 6 | 0.293 | 77.20 |
| 8 | 10 | 0.249 | 59.90 |
| 16 | 5 | 0.180 | 50.40 |

EXAMPLE 8

Preparation of SHNH-IgG Frozen Samples

Vials A and B containing respectively listed contents were prepared according to the following methods:

| | A | B |
|---|---|---|
| Tricine | 200 mg/vial | 80 mg/vial |
| SnCl₂ | 100 μg | 100 μg |
| IgG SHNH | 2 mg/vial | 2 mg/vial |
| Citrate | 3.8 mg | 3.8 mg |
| NaCl | 2.3 mg | 2.3 mg |

A stock solution of 20 mM citrate pH 5.9 was prepared from citric acid and sodium hydroxide. A weighed amount of tricine (6.25 g or 2.5 g) was dissolved into 25 ml of citrate stock. The tricine solution was sparged 20 min. with nitrogen. A stannous chloride stock solution was prepared by dissolving 30 mg of SnCl₂ 2H₂O into 2 ml 0.1N HCl. Two hundred (200) μl of stannous chloride solution were added to 25 ml tricine solution and kept under nitrogen. Eight hundred (800) μl of 10 mg/ml IgG SHNH in 20 mM citrate was gently bubbled with nitrogen and 3.2 ml of tricine/stannous chloride added. Samples were immediately dispensed into 4 nitrogen purged vials, sealed with rubber septa and aluminum crimped caps and frozen at −70° C.

The above methods are repeated with the addition of 0.2 mg/vial polysorbate 80 to the formulations prior to lyophilization.

EXAMPLE 9

SHNH-IgG Frozen Formulations

The methods of Example 8 were repeated with the following SHNH-IgG formulations C and D.

| | C | D |
|---|---|---|
| Tricine | 80 mg/vial | 40 mg/vial |
| SnCl₂ | 100 μg | 50 μg |
| IgG SHNH | — | 2 mg |
| Citrate | 3.8 mg | 3.8 mg |
| NaCl | — | — |
| Glycine | — | — |

The above methods are repeated with the addition of 0.2 mg/vial polysorbate 80 to the formulations prior to lyophilization. The contents of Formulation C above may be separately conjugated to IgG, following reconstitution of the vial C contents.

EXAMPLE 10

SHNH-IgG Formulations

The methods of Example 8 up to the freezing step were repeated with the following formulations E and F of SHNH-IgG:

| | E | F |
|---|---|---|
| Tricine | 80 mg/vial | 80 mg/vial |
| SnCl₂ | 100 μg | 100 μg |
| IgG SHNH | 2 mg/vial | 2 mg/vial |
| Citrate | 3.8 mg | 3.8 mg |
| NaCl | — | — |
| Mannitol | — | — |
| Glycine | — | 20 mg |

The above vials of formulations E and F were filled with 1 mL of solution, frozen at about 0.5° C./min to −50° C. and held below −50° C. for 2 hours. The chamber pressure was reduced to 80 μm Hg and the shelf was ramped at 0.3° C./min to −30° C., and held at this temperature for 21 hours. The shelf was then ramped to 0° C. at 0.5° C./minute and held there for 6 hours. Finally, the chamber pressure was raised to 100 μm Hg and the shelf was ramped to 25° C. at 0.5° C./min and held there for 18 hours. The chamber was then brought to atmospheric pressure with nitrogen and the vials were stoppered and removed from the chamber.

The above methods are repeated with the addition of 0.2 mg/vial polysorbate 80 to the formulations prior to lyophilization.

EXAMPLE 11

Preparation of SHNH-IgG/Tricine/SnCl₂ Lyophilized Kits

Formulations G and H of SHNH-IgG/tricine/SnCl₂ having the composition in the table below was prepared as follows.

| | G | H |
|---|---|---|
| Volume | 0.5 ml | 0.5 ml |
| IgG-SHNH | 1.0 mg | 2.0 mg |
| Citrate Na₃ | 9.3 mg | 9.3 mg |
| Citrate H | 1.8 mg | 1.8 mg |
| tricine | 72 mg | 200 mg |

-continued

|  | G | H |
|---|---|---|
| SnCl$_2$—2H$_2$O | 100 µg | 100 µg |
| pH | 5.6 | 5.6 |

A deaerated bulk solution of citrate/tricine is prepared by weighing the solids (citrate Na, citrate H and tricine ) into a flask of suitable capacity, dissolving the solids in sufficient volume of boiled water such that in formulation G, there is about 166 mg tricine/ml and in formulation H there is about 422 mg tricine/ml, sterile filtering using a 0.22u pore size Millipak filter, sealing the flask with a septum, and sparging with N$_2$.

Upon bulk solution reaching room temperature, solid SnCl$_2$-2H$_2$O is added and dissolved with stirring while sparging with N$_2$. Upon dissolution of the tin, a concentrated deaerated solution of IgG-SHNH is added to render a final solution having a concentration of 2–4 mg/mL IgG-SHNH. Upon addition of protein the solution can be dispensed into 3 ml vials as 0.5 ml aliquots and partially stoppered.

Lyophilization of product is carried out essentially as in Example 10. The product is frozen to a temperature below −35° C. at a rate of about 0.5 degrees C per minute and held there for a couple hours. After sufficient equilibration (e.g., 2 hours), the chamber pressure is reduced to about 80 µm Hg and the shelves are heated to −15° C. to −30° C. at a rate of about 0.3 degrees C per minute and held there while primary drying occurs (approximately 24 hours). After primary drying the shelves are slowly heated to +15° C. to +25° C. at a rate of 0.5 degrees C per minute and secondary drying begun. After lyophilization is complete, the vials are back-flushed with nitrogen and sealed.

EXAMPLE 12

Effect of Polysorbate 80 on Particulates

Particle counts of lyophilized, reconstituted DTPA-IgG of Example 1 was determined on Particle Measuring Systems Model LS-20 Particle Counter. Data demonstrates that the addition of polysorbate 80 (TWEEN 80) minimizes the formation of particulates at both pH 4.5 and pH 6.2. See Table VII. The data also suggests that there is less particulate formation at pH 4.5 with TWEEN 80 (total of 533 particulates between 2 µm and 125 µm) than at pH 6.2 with TWEEN 80 (total of 3322 particulates between 2 µm and 125 µm).

TABLE VII

EFFECT OF EXCIPIENT AND PH ON PARTICLE FORMATION

| Particle Size (µm) | pH 4.5 no TWEEN | pH 4.5 with TWEEN 80 | pH 6.2 no TWEEN | pH 6.2 with TWEEN 80 |
|---|---|---|---|---|
| 2 | 7988 | 353 | 6260 | 2287 |
| 5 | 1290 | 77 | 831 | 414 |
| 7.5 | 788 | 42 | 470 | 293 |
| 9.9 | 353 | 39 | 207 | 186 |
| 12.5 | 101 | 9 | 59 | 82 |
| 15 | 70 | 4 | 39 | 41 |
| 17.5 | 40 | 0 | 18 | 4 |
| 20.5 | 27 | 2 | 19 | 2 |
| 22.5 | 30 | 2 | 12 | 5 |
| 25 | 43 | 0 | 10 | 4 |
| 29.6 | 39 | 1 | 10 | 1 |
| 35 | 30 | 4 | 11 | 1 |
| 50 | 12 | 0 | 6 | 2 |
| 100 | 0 | 0 | 0 | 0 |
| 125 | 0 | 0 | 0 | 0 |

EXAMPLE 13

Effect of pH on Labelling Efficiency

Labeling efficiency was determined on lyophilized, reconstituted DTPA-IgG formulation of Example 1. Data demonstrates that indium chloride labelling efficiency at 1 hour is higher at pH 4.5 than at pH 6.2 for lyophilized DTPA-IgG formulations both with and without TWEEN 80 Table III demonstrates the labeling efficiency both in the presence and absence of TWEEN 80, and at pH 4.5 and 6.2. See Table VIII. The labeling procedure was performed by admixing 2 ml sterile saline to the vials containing 2.0 mg imaging agent as recited in Example 1 herein, with and without polysorbate ("TWEEN") 80, and at pH 4.6 and 6.2, thereby reconstituting the lyophilized product. 1.4–2.6 mCi of 111InCl (10 mCi/ml) was then added to the vial and the mixture incubated at RT for 15 minutes.

TABLE VIII

EFFECT OF EXCIPIENT AND PH ON LABELING EFFICIENCY

| Formulation | Labeling Efficiency |
|---|---|
| pH 6.2, no TWEEN | 73% |
| pH 6.2 with TWEEN 80 | 81% |
| pH 4.5, no TWEEN | 98% |
| pH 4.5 with TWEEN 80 | 97% |

EXAMPLE 14

Lyophilization of SHNH-Chemotactic Peptide—I

Lyophilized chemotactic peptide imaging agent was prepared Ps follows. N-For-Norleucyl-Leucyl-Phenylalanyl-Lysine-NH$_2$, (SEQ ID NO: 3) N-For-Methionyl-Leucyl-Phenylalanyl-Lysine, (SEQ ID NO: 4) N-For-Methionyl-Leucyl-Phenylalanyl-diaminohexyl amide, and N-For-Methionyl-Leucyl-Phenylalanyl-D-Lysine-NH$_2$ (SEQ ID NO: 5) were synthesized and purified by standard solid phase techniques (Merrifield, R. B., *J. Am. Chem. Soc.* 15:2149–2154 (1963); Stewart, J. M., and Young, J. D., *Solid Phase Peptide Synthesis*, W.H. Freeman & Company, San Francisco, Calif. (1969)) as described by Fischman, A. J., *J. Nucl. Med.* 32:483–491 (1991). All reagents were obtained as the highest available grade from commercial sources. The nicotinyl hydrazine conjugation of these compounds was performed as follows.

To 186 mg of N-For-Met-Leu-Phe-diaminohexyl amide was added 2 mL of dimethylformamide (DMF) and 60 µL diisopropylethylamine, followed by 154 mg succinamidyl-6-t-Boc-hydrazinopyridine-3-carboxylicacid (Abrams, M. J., et al.,*J. Nucl. Med.* 31:2022–2028 (1990) in 1 mL DMPF. The mixture became yellow and the peptide dissolved within a short time. After 2 hours, ether-pet ether was added to the reaction mixture and the upper layer was discarded. Water was added to the oily residue causing a solid to form. The solid was washed with 5% sodium bicarbonate, water, and ethyl acetate yielding a product weighing 183 mg. The t-BOC protecting group was removed by stirring the crude product for 15 minutes at 20° C. with 5 mL of trifluoroacetic acid (TFA) containing 0.1 mL p-cresol. Prolonged treatment with TFA resulted in increased levels of a side product. The TFA was removed by rotary evaporation and ether was added to the residue to precipitate the deprotected peptide. The product was purified by reverse phase HPLC on a 2.5×50 cm Whatman ODS-3 column eluted with a gradient of acetonitrile in 0.1% TFA. Fractions containing the major component were combined and the solvent removed to yield the desired product.

The resulting SHNH-derivatized chemotactic peptide product (0.2 mg) is admixed with 2.6 mg of maltose, 0.02 mg of polysorbate 80 in 1 mL of 20 mM citrate buffer. The formulation is lyophilized in accordance with the methods of Example 11 herein.

EXAMPLE 15

Lyophilization of SHNH-Chemotactic Peptide—II

The chemotactic peptide N-formyl-Nle-Leu-Phe-Nle-Tyr-Lys (SEQ ID NO: 1) was synthesized using standard solid phase methods well-known in the art (Merrifield, R. B., *J. Am. Chem. Soc.* 15:2149–2154 (1963); Stewart, J. M. and Young, J. D., *Solid Phase Peptide Synthesis*, W.H. Freeman & Company, San Francisco, Calif. (1969)). The epsilon amino group of the C-terminal lysine was modified with DTPA using a cyclic anhydride using standard techniques.

The linker-chemotactic peptide (0.2 mg) was admixed with 0.2 mg of maltose, 0.02 mg of polysorbate 80 in 1 mL of 20 mM citrate buffer. The formulation is lyophilized in accordance with the methods of Example 11.

The above methods were repeated using 2.6 mg tricine instead of maltose, and the formulation lyophilized in accordance with the methods of Example 11.

The above method was repeated substituting 2.6 mg of tricine for 0.2 mg maltose, and repeated substituting 80 mg of tricine for 0.2 mg maltose.

EXAMPLE 16

99mTc Labeling of Hynic Derivitized Chemotactic Peptides

99mTc-pertechnetate (99Mo/99mTc-generator) and stannous glucoheptonate (Glucoscan) are obtained from New England Nuclear (Boston, Mass.). 99mTc-glucoheptonate is used to provide the necessary Tc(V) oxo species for radiolabeling the lyophilized hydrazinonicotinamide conjugated peptides of Example 15 herein. To the freeze-dried kit is added approximately 2.5 mL of 99mTc pertechnetate in 0.9% NaCl. The final radioactive concentration is 5–10 mCi/mL and radiochemical purity of the product is determined by instant thin-layer silica gel chromatography (ITLC-sg) using both acetone and 0.9% NaCl as mobile phase solvents.

The following procedure is used to radiolabel the chemotactic peptide analogs of Example 15 with 99mTc. Approximately 0.2 mg peptide is dissolved in 50 μl dimethylsulfoxide and the solution is diluted to a final concentration of 0.1 mg/mL with 0.1 M acetate buffer pH 5.2. One half milliliter of peptide solution is placed in a clean glass vial and 0.5 mL of 99mTc-glucoheptonate is added. The mixture is vortexed briefly and allowed to stand at room temperature for 1 hour. Radiochemical purity is determined by ITLC-sg in three solvent systems: acetone, 0.9% NaCl, and acetone:water (9:1).

The above labeling is repeated, employing SHNH-IgG in place of SHNH-chemotactic peptide.

---

We claim:

1. An imaging agent composition comprising a targeting molecule, the excipient polysorbate 80, a linker and a drying protectant, wherein the composition has a pH of about 3.0–6.5, and wherein said targeting molecule comprises a chemotactic peptide.

2. The composition of claim 1 wherein the linker is DTPA or SHNH.

3. The composition of claim 1 wherein the drying protectant is a saccharide.

4. The composition of claim 3 wherein the saccharide is maltose or mannitol.

5. The composition of claim 4 wherein the drying protectant is present in a weight percent of lyophilized product of about 500% to 2000%.

6. The composition of claim 1 wherein the drying protectant is tricine.

7. The composition of claim 6 wherein the weight ratio of targeting molecule to tricine is about 1:5 to 1:500.

8. The composition of claim 1 wherein the linker is DTPA and wherein the composition additionally comprises a citrate buffer.

9. The composition of claim 1 wherein the linker is SHNH and wherein the composition additionally comprises a citrate buffer, and wherein the drying protectant is tricine.

10. The composition of claim 9 wherein the weight ratio of chemotactic peptide to tricine is about 1:5 to about 1:500.

11. An imaging agent composition comprising chemotactic peptide, SHNH, stannous chloride, polysorbate 80, tricine and citrate buffer.

12. The composition of claim 10 wherein the tricine is present in a weight ratio of chemotactic peptide to tricine of about 1:5 to 1:500, and wherein the pH of the composition is about 5.2–5.5.

13. The composition of claim 12 wherein the composition is frozen at about –40 to –70 C.

14. The composition of claim 12 wherein the polysorbate 80 is present in a weight percent of chemotactic peptide of about 1000%.

15. The composition of claim 14 wherein the composition is frozen at about –40 to –70 C.

16. A lyophilized imaging agent composition comprising a targeting molecule, the excipient polysorbate 80, a linker and a drying protectant and a citrate buffer, wherein said targeting molecule comprises a chemotactic peptide.

17. The composition of claim 16 wherein the linker is DTPA or SHNH.

18. The composition of claim 16 wherein the drying protectant is a saccharide.

19. The composition of claim 18 wherein the saccharide is maltose or mannitol.

20. The composition of claim 19 wherein the drying protectant is present in a weight percent of lyophilized product of about 500% to 2000%.

21. The composition of claim 16 wherein the drying protectant is tricine.

22. The composition of claim 20 wherein the weight ratio of targeting molecule to tricine is about 1:5 to about 1:500.

23. The composition of claim 22 wherein the linker is DTPA and wherein the composition additionally comprises a citrate buffer.

24. A pharmaceutical composition comprising the composition of claim 23 and a pharmaceutically acceptable carrier or diluent.

25. The composition of claim 21 wherein the linker is SHNH, wherein the targeting molecule is a chemotactic peptide, and wherein the composition additionally comprises a citrate buffer.

26. The composition of claim 25 wherein the weight ratio of chemotactic peptide to tricine is about 1:5 to about 1:500.

27. A pharmaceutical composition comprising the composition of claim 26 and a pharmaceutically acceptable carrier or diluent.

28. A lyophilized imaging agent composition comprising chemotactic peptide, SHNH, stannous chloride, the excipient polysorbate 80, tricine and citrate buffer.

29. The composition of claim 28 wherein the tricine is present in a weight ratio of chemotactic peptide to tricine of about 1:5–1:500.

30. A pharmaceutical composition comprising the composition of claim 29 and a pharmaceutically acceptable carrier or diluent.

31. The composition of claim 29 wherein the polysorbate 80 is present in a weight percent of chemotactic peptide of about 1000%.

32. A pharmaceutical composition comprising the composition of claim 31 and a pharmaceutically acceptable carrier or diluent.

33. A method for preparing an imaging agent composition, comprising:
(a) preparing the lyophilized composition of claim 16; and
(b) admixing the lyophilized composition with a pharmaceutically acceptable carrier or diluent.

34. A kit comprising a two-vial system of lyophilized imaging agent composition of claim 16 and aqueous diluent, comprising:
(a) a first vial comprising lyophilized imaging agent; and
(b) a second vial comprising a pharmaceutically acceptable carrier or diluent.

35. The kit of claim 34 wherein the imaging agent comprises SHNH, chemotactic peptide, tricine, stannous chloride and citrate, and wherein the diluent comprises sterile sodium chloride.

* * * * *